(12) United States Patent
Cunin et al.

(10) Patent No.: US 9,694,074 B2
(45) Date of Patent: Jul. 4, 2017

(54) FUNCTIONALIZED POROUS SILICON NANOPARTICLES AND USE THEREOF IN PHOTODYNAMIC THERAPY

(71) Applicants: CENTRE NATIONAL DE LA RECHERCHE SCIENTIFIQUE (CNRS), Paris (FR); UNIVERSITE MONTPELLIER 2 SCIENCES ET TECHNIQUES, Montpellier (FR); THE REGENTS OF THE UNIVERSITY OF CALIFORNIA, Oakland, CA (US); ECOLE NATIONALE SUPERIEURE DE CHIMIE DE MONTPELLIER, Montpellier (FR)

(72) Inventors: Frederique Cunin, Montpellier (FR); Jean-Olivier Durand, Palavas-les-Flots (FR); Michael J. Sailor, La Jolla, CA (US); Marcel Garcia, Prades-le-Lez (FR); Emilie Secret, Montpellier (FR); Magali Gary-Bobo, Castelnau-le-Lez (FR); Marie Maynadier, Ceyras (FR); Alain Morere, Saint-Gely du Fesc (FR)

(73) Assignees: CENTRE NATIONAL DE LA RECHERCHE SCIENTIFIQUE (CNRS), Paris (FR); UNIVERSITE MONTPELLIER 2 SCIENCES ET TECHNIQUES, Montpellier (FR); THE REGENTS OF THE UNIVERSITY OF CALIFORNIA, Oakland, CA (US); ECOLE NATIONALE SUPERIEURE DE CHIMIE DE MONTPELLIER, Montpellier (FR)

( * ) Notice: Subject to any disclaimer, the term of this patent is extended or adjusted under 35 U.S.C. 154(b) by 0 days.

(21) Appl. No.: 14/388,860

(22) PCT Filed: Mar. 26, 2013

(86) PCT No.: PCT/EP2013/056423
§ 371 (c)(1),
(2) Date: Sep. 29, 2014

(87) PCT Pub. No.: WO2013/144154
PCT Pub. Date: Oct. 3, 2013

(65) Prior Publication Data
US 2015/0087050 A1 Mar. 26, 2015

(30) Foreign Application Priority Data

Mar. 27, 2012 (FR) .................. 12 52703

(51) Int. Cl.
| | | |
|---|---|---|
| *A61K 41/00* | (2006.01) | |
| *A61K 31/28* | (2006.01) | |
| *A61K 31/315* | (2006.01) | |
| *A61K 31/409* | (2006.01) | |
| *A61N 5/06* | (2006.01) | |
| *C09B 47/00* | (2006.01) | |

(52) U.S. Cl.
CPC .......... *A61K 41/0071* (2013.01); *A61K 31/28* (2013.01); *A61K 31/315* (2013.01); *A61K 31/409* (2013.01); *A61K 41/008* (2013.01); *A61N 5/062* (2013.01); *C09B 47/00* (2013.01); *Y10T 428/2982* (2015.01)

(58) Field of Classification Search
CPC .............. A61K 41/0071; A61K 41/008; A61K 31/409; A61K 31/28; A61K 31/315; A61N 5/062; C09B 47/00; Y10T 428/2982
See application file for complete search history.

(56) References Cited

U.S. PATENT DOCUMENTS

| | | | |
|---|---|---|---|
| 8,425,879 B2 * | 4/2013 | Brevet ................ | C07D 487/22 424/400 |
| 2011/0262357 A1 * | 10/2011 | Brevet ................ | C07D 487/22 424/9.1 |

OTHER PUBLICATIONS

David Brevet, et al., "Mannose-targeted mesoporous silica nanoparticles for photodynamic therapy", Chemical Communications, 2009, Issue 12, 1475-1477.*
Ouahiba Hocine, et al., "Silicalites and Mesoporous Silica Nanoparticles for photodynamic therapy", International Journal of Pharmaceutics 402 (2010) 221-230.*
Ling Xiao, et al., "Porous Silicon Nanoparticle Photosensitizers for Singlet Oxygen and Their Phototoxicity against Cancer Cells", ACS Nano, 2011, 5(5), 3651-3659.*
Michael J. Sailor and Elizabeth C. Wu, "Photoluminescence-Based Sensing With Porous Silicon Films, Microparticles, and Nanoparticles", Advanced Functional Materials 2009, 19, 3195-3208.*
Emilie Secret, Marie Maynadier, Audrey Gallud, Magali Gary-Bobo, Arnaud Chaix, Emmanuel Belamie, Philippe Maillard, Michael J. Sailor, Marcel Garcia, Jean-Olivier Durand and Frederique Cunin, "Anionic porphyrin-grafted porous silicon nanoparticles for photodynamic therapy", Chemical Communications, 2013, 49, 4202-4204.*

*Primary Examiner* — John Pak
*Assistant Examiner* — Nathan W Schlientz
(74) *Attorney, Agent, or Firm* — Young & Thompson

(57) ABSTRACT

Disclosed are nanovectors of formula (I) that can be used simultaneously for the targeting, imaging and treatment, by photodynamic therapy, of cancer cells, and to biodegradable silicon nanoparticles containing a variety of photosensitizing molecules, in particular porphyrins, capable of targeting diseased cells and inducing cell death by excitation in the near-infrared region (>600 nm) in monophotonic and biphotonic modes. In formula (I), (AA) is a porous silicon nanoparticle.

18 Claims, 22 Drawing Sheets

2A                                    2B 3A  3B a)

b)

c)

d)

e)

FUNCTIONALIZED POROUS SILICON NANOPARTICLES AND USE THEREOF IN PHOTODYNAMIC THERAPY

This invention has been produced with the support of the United States government under grant No. DMR-0806859 awarded by the National Science Foundation. The United States government holds certain rights over the invention.

The present invention relates to nanovectors that can be used simultaneously for the targeting, imaging and treatment, by means of photodynamic therapy, of cancer cells. In particular, it relates to novel biodegradable silicon-based nanoparticles containing a variety of photosensitizing molecules which are capable of targeting diseased cells and inducing cell death by means of excitation in the near infrared (>600 nm) in monophotonic and biphotonic modes. The invention also relates to a method for treating certain pathologies, and in particular cancers, comprising administering biodegradable silicon-based nanoparticles containing at least one photosensitizing molecule and at least one targeting molecule, this administration being followed by treatment with infrared irradiation.

Photodynamic therapy is based on the use of certain therapeutic molecules called photosensitizers which, when activated by means of a light source of a suitable wavelength, in the visible or near-infrared range, transmit their excess energy to the molecular oxygen surrounding them. These photosensitizers are usually combined with targeting molecules in such a way that they preferably come to be located in malignant tissues. When it is activated by light, the photosensitizing therapeutic agent converts the molecular oxygen in the triplet ground state ($^3O_2$) to highly cytotoxic singlet oxygen ($^1O_2$), and to other reactive oxygen species ($O_2^{\bullet-}$, $OH^\bullet$). These reactive oxygen species, and more particularly singlet oxygen, are toxic to the cells surrounding them and lead to the destruction of the cancer tissues in their immediate surroundings: they oxidize the cell membranes and thus lead to irreversible damage to the cells containing the photosensitizer. This is a promising treatment that has been used clinically for some ten years. The advantages of photodynamic therapy are the possibility of repeating the treatments without accumulated toxicity (compared with radiotherapy), its low cost, its ease of use, and its applicability to a large number of diseases (cardiovascular, dermatological and ophthalmic). As the treatment requires light in order to be effective, it is localized and displays little systemic toxicity. In the case of malignant tumours, photodynamic therapy can be more effective and less distressing than other therapies.

Photodynamic therapy is based on a double selectivity: firstly the selective irradiation of the tissues involved and secondly the selectivity relating to the photosensitizer for the target tissues. In the absence of irradiation, as photosensitizers are of low toxicity for cells, their diffusion in the organism only leads to a few drawbacks.

In order to be able to be used in vivo, a photosensitizer must have several qualities and, in particular, it must be able to be easily vectorized to the cancer tissues, it must be water-soluble, easy to produce, non-toxic in the absence of irradiation, stable vis-à-vis circulating enzymes, having good tropism for the tumour cells, and it must be quickly eliminated from healthy tissues. Another constraint of these formulations is the ability to preserve the effectiveness of the photosensitizers, i.e. their ability to convert the molecular oxygen that surrounds them to reactive oxygen species. In fact, certain formulations interact with the excited states of the photosensitizer and reduce its effectiveness.

STATE OF THE PRIOR ART

Current treatments for diseases and cancers with a therapy using the generation of oxidizing species (ROS and singlet oxygen), such as photodynamic therapy, are carried out by photoexcitation of porphyrin-type photosensitizing organic molecules. The use of these photosensitizing organic molecules, however, is subject to the following limitations: the photosensitizing organic molecules are hydrophobic, and require a delivery system for clinical use, in particular specific formulations, especially in the form of colloidal suspensions, liposomes, nanoparticles. These molecules do not target the tumour cells effectively, they have a significant residence time in "normal" tissues and can be activated by visible light, which causes side effects of destroying the healthy cells of the superficial tissues (skin, eye) by exposure to ambient light and a prolonged photosensitivity of the patients.

The ideal photosensitizer system must have firstly a high quantum yield of singlet oxygen and ROS, secondly a substantial optical conversion at long wavelengths (700-1200 nm), thirdly minimal toxicity in the dark and toxicity in visible and UV light that is minimal over time, fourthly a preferred localization in the diseased cells.

A promising approach developed by a good number of researchers to overcome the difficulties listed above is to incorporate the photosensitizing molecules (porphyrins and others) in ceramic, silica, oxide or polymer nanoparticles. The nanoparticles of these materials used as host system make it possible in particular to improve the bioavailability of the hydrophobic photosensitizing molecules and the targeting using specific ligands the receptors of which are overexpressed in the diseased cells.

Several documents describe mesoporous silica nanostructures for therapeutic and targeting applications. In particular, WO 2011073054 and FR 2935974 describe porous silica nanoparticles which are obtained by the sol-gel route for therapeutic applications and in photodynamic therapy, but do not have the physical properties of the porous silicon nanoparticles of the invention. The porphyrins used in FR 2935974 are similar to the porphyrins used in the present invention, but in the provisions of FR 2935974 the nanostructures in which these porphyrins are incorporated cannot be excited in the near infrared (in monophotonic and biphotonic modes).

Silica is a form of silicon dioxide $SiO_2$ that is found in nature, whereas porous silicon is prepared from crystalline silicon, a semiconductor material. When silicon has been made mesoporous, and therefore structured on the nanoscale, it has unique physical, in particular optical, properties (photoluminescence, etc.) due to quantum confinement effects. These electronic and physical properties do not exist for a porous silica, which is an amorphous electronic insulator material.

Several documents describe porous silicon-based microstructures and nanostructures for therapeutic and targeting applications. In particular, WO 2010096733, WO 2009009563 and WO 2006050221 describe porous silicon microstructures and nanostructures for therapeutic applications, vectorization of molecules and imaging, but do not describe a transfer of energy from the porous silicon to photosensitizing molecules, nor an application in photodynamic therapy. Ji-Ho Park et al., Nature Materials, 8 Apr. 2009, 331-336 describes the use of porous silicon nanoparticles for the visualization of tumour tissues by luminescence. The luminescent porous silicon nanoparticles can be excited in the infrared and in particular by biphotonic excitation.

A photosensitizer based on CdSe Qdot and porphyrin has been described in J. Mater. Chem., 2011, 21, 2455-2458. This material can be used in biphotonic irradiation mode for applications in dynamic phototherapy. However, the use of cadmium poses problems of toxicity.

The 2011 Euromat paper, Montpellier, France, E. Secret et al., "Porous silicon nanoparticles functionalized for photodynamic therapy" describes the grafting of mannose onto porous silicon nanoparticles and the grafting of a porphyrin on hydrosilylated porous silicon nanoparticles functionalized by undecylenic acid. However, the grafting method used is not satisfactory, to the extent that it was observed that the grafting of the porphyrin was not sufficiently stable and did not allow the satisfactory transport of the photosensitizer to the target cells. Moreover, this document neither mentions nor suggests a transfer of energy from the porous silicon to photosensitizing molecules and/or the possibility of biphotonic excitation.

The inventors were therefore surprised to discover that porous silicon nanoparticles comprising at least one covalently grafted photosensitizing molecule, such as a porphyrin for example, were capable of being excited in the near infrared, in monophotonic and biphotonic modes, and could therefore be used in photodynamic therapy treatments. In particular, the inventors suggest that in such nanoparticles, when they are subjected to excitation in the near infrared, a transfer of energy is brought about from the porous silicon to the photosensitizing molecules. Moreover, these nanoparticles can also be grafted with targeting molecules which allow a specificity of action against cancer cells.

SUMMARY OF THE INVENTION

A first subject of the invention consists of nanoparticles corresponding to formula (I):

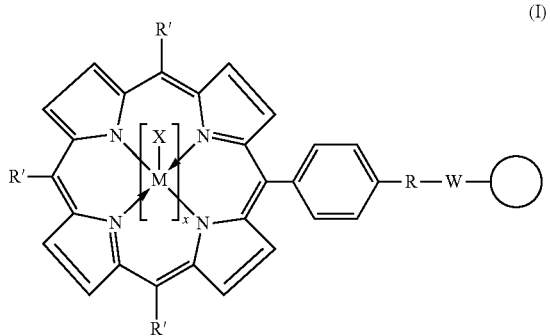

(I)

in which:

represents a porous silicon nanoparticle,
x represents an integer chosen from: 0 and 1,
M represents a metal atom chosen from the transition metals,
X represents a group chosen from: a halide, an anion of a pharmaceutically acceptable carboxylic acid,
R represents a group chosen from: a urea (—NH—CO—NH—), a thiourea (—NH—CS—NH—),
W represents a C1-C12 alkanediyl group,
R' represents a group chosen from:

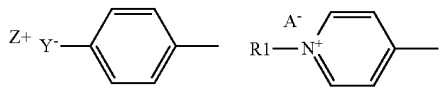

$Z^+$ represents a pharmaceutically acceptable organic or mineral cation,
$Y^-$ represents a group which can be chosen from: —COO$^-$, —SO$_3^-$
$A^-$ represents an anion which can be chosen from: a halide, an anion of a pharmaceutically acceptable carboxylic acid,
R1 represents a C1 to C10 alkyl.

According to a preferred embodiment, the nanoparticles correspond to formula (Ia):

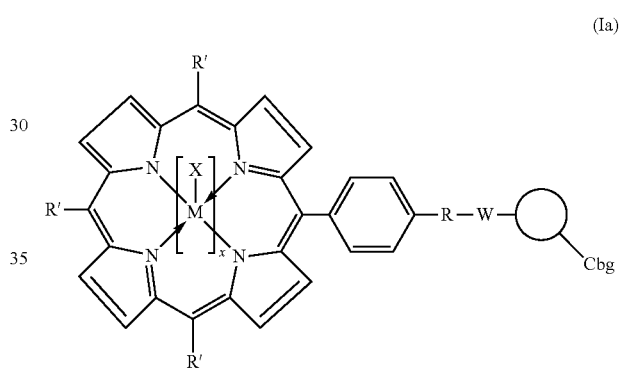

(Ia)

In which Cbg represents a specific targeting molecule for neoplastic tissues.

According to a preferred embodiment, the nanoparticles have a size ranging from 20 to 200 nm, advantageously from 50 to 190 nm, better still from 100 to 175 nm, and preferably from 140 to 160 nm, and the pore size ranges from 5 to 50 nm, advantageously from 10 to 30 nm According to a preferred embodiment, in formulae (I) and (Ia) x represents 0.

According to a preferred embodiment, in formulae (I) and (Ia) one or more of the following characteristics are satisfied:

X represents a group chosen from: Cl$^-$, Br$^-$, I$^-$, acetate, propionate, butyrate, ascorbate, benzoate, cinnamate, citrate, fumarate, glycolate, malonate, tartrate, malate, maleate, mandelate, tosylate, W represents a —(CH$_2$)$_3$— group.

R1 represents a group chosen from: a C1-C3 alkyl, $Z^+$ represents a cation which can be chosen from: K$^+$, Li$^+$, Na$^+$, NH$_4^+$, A represents an anion which can be chosen from: Cl$^-$, Br$^-$, I$^-$, acetate, propionate, butyrate, ascorbate, benzoate, cinnamate, citrate, fumarate, glycolate, malonate, tartrate, malate, maleate, mandelate, tosylate, R' is chosen from:

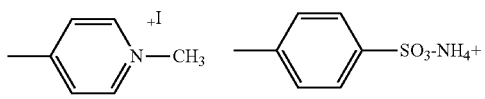

Cbg, if present, is chosen from sugars and derivatives of sugars.

The preferred nanoparticles are chosen from:

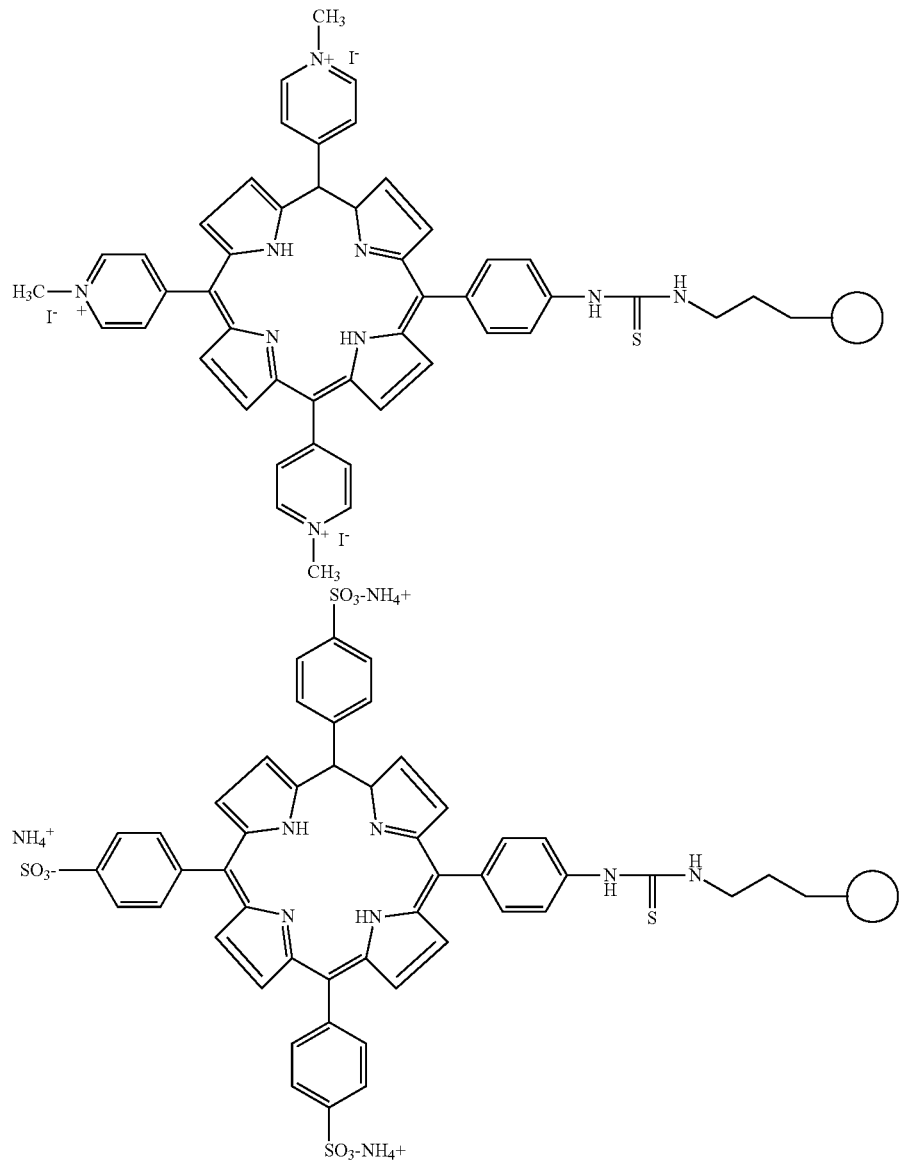

The invention also relates to a method for producing nanoparticles, comprising the steps of:
(i) providing porous silicon nanoparticles,
(ii) functionalizing the porous silicon nanoparticles with groups comprising at least one $NH_2$ function or at least one isocyanate, isothiocyanate or semicarbazide function
(iii) providing and grafting a photosensitizing molecule, which bears a group complementary to the one borne by the nanoparticle, so as to form a urea or thiourea bond, and optionally
(iv) grafting with at least one targeting molecule.

According to a preferred variant, the method comprises the steps of:
(i) a—electrochemical etching of monocrystalline silicon plates in a hydrofluoric acid (HF) ethanol solution,
    b—removal of the porous film and treatment by ultrasound,
(ii) a—controlled oxidation followed by silanization so as to produce Si—OH groups and $SiO_2$ species on the surface of the porous silicon nanoparticles, and/or
    b—hydrosilylation,
(iii) grafting the nanoparticles with a porphyrin-type photosensitizing molecule corresponding to formula (II), in which Q represents a group chosen from: —$NH_2$, —N=C=O, —N=C=S,

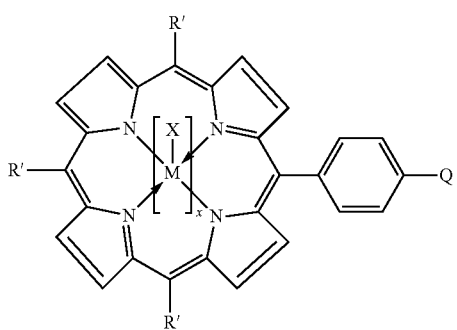
(II)

(iv) grafting the nanoparticles with a sugar or a sugar derivative, with the aid of a phenylsquarate group or a semicarbazone group.

The invention also relates to nanoparticles described above for the use thereof to detect, treat, monitor, prevent, delay the appearance and/or recurrence of a pathology chosen from cancers, tumours, cell proliferation diseases, skin diseases.

It also relates to a medicinal composition comprising nanoparticles as described above in a pharmaceutically acceptable support.

It also relates to a cosmetic composition comprising nanoparticles as described above in a pharmaceutically acceptable support.

It also relates to a kit for the detection, treatment, monitoring, prevention, delay of the appearance and/or recurrence of a pathology chosen from cancers, tumours, cell proliferation diseases, comprising:

porous silicon nanoparticles grafted via a covalent bond with at least one photosensitizing molecule, or a medicinal composition comprising them
and
means that allow a biphotonic irradiation in the infrared.

In particular, the invention relates to a kit for the detection, treatment, monitoring, prevention, delay of the appearance and/or recurrence of a pathology chosen from cancers, tumours, cell proliferation diseases, comprising:

nanoparticles as defined above, or a composition as defined above,
and
means that allow an irradiation in the infrared.

The invention relates to therapeutic agents and devices for the non-invasive treatment of a large number of diseases and cancers.

The invention relates in particular to biodegradable and non-toxic porous silicon nanostructures or nanoparticles carrying photosensitizing organic molecules. The porous silicon nanostructures allow the photosensitizing molecules to produce strongly cytotoxic oxidizing species, including singlet oxygen, when they are irradiated with near-infrared light (in monophotonic and/or biphotonic mode) for the non-invasive treatment of various diseases including cancer. The presence of the host nanostructures of porous silicon allows the photosensitizing molecules to generate oxidizing species by photoexcitation in the near infrared. When they are insulated or encapsulated in other types of host materials, such as the materials with which they are combined in the prior art, these photosensitizing molecules cannot be excited in the near infrared at powers that are acceptable for a living organism. They can be excited in biphotonic mode, but at very high powers, which produces photo-damage to tissues. The use of near-infrared light has the advantage of allowing a greater penetration into the living tissues than other wavelengths of light, for a non-invasive therapeutic treatment. The porous silicon nanostructures of controlled size and texture are prepared by the electrochemical, sonication and filtration route. The photosensitizing molecules are bonded to the host nanostructures covalently by new grafting chemistries on this type of host material. Agents for targeting diseased cells can also be grafted, or not, onto the porous silicon nanostructures by novel methods. These multifunctional nanostructures are internalized in vitro by the cancer cells. The oxidizing species and singlet oxygen generated by excitation in the near infrared (750 nm, biphotonic mode) irreversibly destroy the diseased cells.

The invention makes it possible to use near-infrared light (>600 nm) for the excitation of porous silicon nanoparticles containing photosensitizing molecules that generate oxidizing species (including singlet oxygen) with the aim of inducing cell death. Thanks to its quantum confinement properties, porous silicon can be subjected to energy transfer reactions. These energy transfer processes can be very effective because of the long lifetimes (microseconds) of the excitons, and because of the large specific surface area. The porous silicon itself can also generate oxidizing species (ROS and singlet oxygen).

The benefit of excitation in the near infrared is the greater penetration into the tissues by the light, which allows the treatment of various diseases and of cancer in deeper tissues, with the possibility of a non-invasive therapy. The excitation in the near infrared also makes it possible to limit the side effects due to the light in the tissues treated by photodynamic therapy.

The invention allows the encapsulation and vectorization of the photosensitizing molecule. The photosensitizing molecules are covalently bonded to the porous silicon nanoparticles. This bond was made possible by the development of a suitable covalent grafting method. The porous silicon nanoparticles are also modified by targeting molecules which allow them to selectively recognize target cells in vivo.

The covalent grafting of the photosensitizing molecules using novel chemistries described in the invention makes it possible to control the vectorization of these photosensitizing molecules to the target cells thanks to the targeting using specific ligands the receptors of which are overexpressed in the diseased cells, and it also makes it possible to improve the bioavailability of the hydrophobic molecules by their encapsulation.

The porous silicon nanoparticles offer a large specific surface area with the ability to bond and be loaded with several, identical or different, molecules or complexes which are delivered to the tissues in vivo.

Moreover, their luminescent properties allow a monitoring of their presence in the organism and a use in diagnosis.

When they are present in a quantity compatible with therapeutic applications, the porous silicon nanoparticles can circulate in the blood for several days with no evidence of toxicity. The non-functionalized porous silicon particles alone do not induce a toxic response that is unacceptable for envisaging the clinical use thereof.

The porous silicon nanoparticles are biocompatible and biodegradable, and degrade into compounds eliminated by renal clearance with an absence of toxicity. Porous silicon is a very attractive alternative to the other Qdot-type nanostructured semiconductors, based on heavy metals, which have beneficial quantum confinement properties, but are very toxic. Trace silicon is an element necessary for bone growth and collagen. The final degradation products of porous silicon are oxoanions of orthosilicic acid, $Si(OH)_4$. They constitute the bioavailable forms of silicon. Orthosilicic acid is naturally present in a number of tissues and an excess of silicic acid will be effectively eliminated from the body by the kidneys. Porous silicon has very advantageous properties for in vivo applications: its low toxicity, its specific surface area, its pores and its pore volume of variable size, its compatibility with the growth of cells. The porous silicon nanoparticles meet the specifications of the ideal photosensitizer system (encapsulation, vectorization, excitation in the near infrared, limited sensitivity to light).

The invention allows the biodegradation and the elimination of the porous silicon with controlled kinetics of the host vector particles.

The syntheses needed to produce the invention take little time and are easy to implement.

DETAILED DESCRIPTION

The Nanoparticles

The invention relates to nanoparticles corresponding to formula (I) below

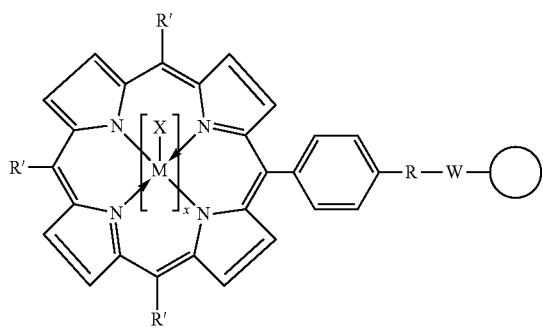

(I)

in which:

represents a porous silicon nanoparticle, x represents an integer chosen from: 0 and 1, M represents a metal atom chosen from the transition metals, X represents a group chosen from: a halide, an anion of a pharmaceutically acceptable carboxylic acid, R represents a group chosen from: a urea (—NH—CO—NH—), a thiourea (—NH—CS—NH—), W represents a C1-C12 alkanediyl group, R' represents a group chosen from:

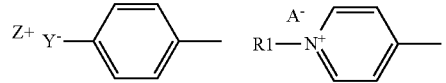

$Z^+$ represents an organic cation or pharmaceutically acceptable mineral, $Y^-$ represents a group which can be chosen from: —COO$^-$, —SO$_3^-$ $A^-$ represents an anion which can be chosen from: a halide, an anion of a pharmaceutically acceptable carboxylic acid, R1 represents a C1 to C10 alkyl.

In formula (I), only the grafting with a porphyrin is shown, but the definition of this formula includes the possibility of a grafting with other groups, such as targeting molecules for example.

By "porous silicon nanoparticles" is meant porous structures with a size ranging from 1 nm to 900 nm, based on silicon. The porous silicon nanoparticles are known, as are methods for producing them. The following documents describe porous silicon nanoparticles that can be used in the present invention, as well as a method for preparing them: WO 2010096733, WO 2009009563 and WO 2006050221, Ji-Ho Park et al., Nature Materials, 8 Apr. 2009, 331-336. Preferably, the size of the porous silicon nanoparticles is from 20 to 200 nm, advantageously from 50 to 190 nm, better still from 100 to 175 nm, and preferably from 140 to 160 nm. The size of the nanoparticles is measured by dynamic light scattering (DLS), scanning electron microscopy (SEM) and transmission electron microscopy (TEM). The size of the pores preferably has a value ranging from 5 nm to 50 nm, advantageously from 10 nm to 30 nm. The size of the pores can be measured by scanning electron microscopy (SEM) and nitrogen adsorption/desorption analysis.

A C1-C10 alkyl group is a linear, branched or cyclic hydrocarbon chain comprising 1 to 10 carbon atoms.

When x represents 0, the compound of formula (I) is a derivative of porphyrin and the groups (M-X) are replaced by two hydrogen atoms. When x represents 1, the compound of formula (I) is a derivative of metalloporphyrin.

According to a variant of the invention represented by formula (Ia), the nanoparticle of formula (I) also comprises at least one targeting molecule Cbg.

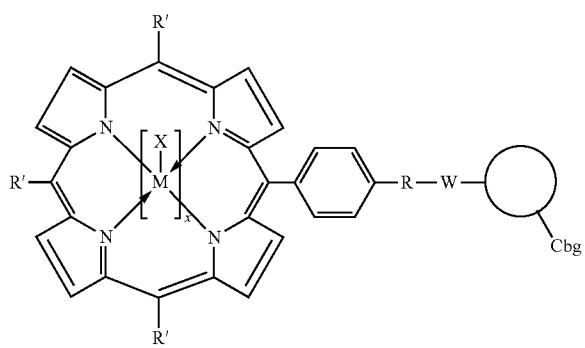

(Ia)

Cbg is preferably chosen from the specific targeting molecules for neoplastic tissues, i.e. biomolecules the receptors of which are overexpressed by cancer cells, or on the surface of cancer cells. In general, the targeting molecules Cbg can be chosen from: folic acid, peptides, carbohydrates, antibodies.

To simplify the representation, only one porphyrin and one targeting molecule are shown in formulae (I) and (Ia). However, the invention defined by formulae (I) and (Ia) includes the grafting of several, identical or different, porphyrins and of several, identical or different, targeting molecules on a silicon nanoparticle.

In formulae (I) and (Ia), the variables defined above are advantageously chosen, independently, according to the following rules:

According to a first preferred variant, x represents 0.

When x represents 1, M preferably represents a metal atom chosen from: Zn, Pt, Pd, Mn, Gd, Ni, Cr, Ru. M is preferably chosen from Pd and Zn.

X preferably represents a group chosen from: Cl$^-$, Br$^-$, I$^-$, acetate, propionate, butyrate, ascorbate, benzoate, cinnamate, citrate, fumarate, glycolate, malonate, tartrate, malate, maleate, mandelate, tosylate and, more preferably still: Cl$^-$, Br$^-$, I$^-$, acetate, tosylate.

W preferably represents a —(CH$_2$)$_3$— group.

R1 advantageously represents a group chosen from: a C1-C3 alkyl, such as for example methyl, ethyl, n-propyl, isopropyl and, more advantageously still, methyl.

Z$^+$ preferably represents a cation which can be chosen from: K$^+$, Li$^+$, Na$^+$, NH$_4^+$.

A$^-$ preferably represents an anion which can be chosen from: Cl$^-$, Br$^-$, I$^-$, acetate, propionate, butyrate, ascorbate, benzoate, cinnamate, citrate, fumarate, glycolate, malonate, tartrate, malate, maleate, mandelate, tosylate and, more preferably still: Cl$^-$, Br$^-$, F$^-$, acetate, tosylate.

R' is preferably chosen from:

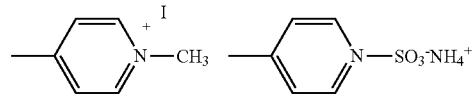

Among the targeting molecules Cbg which can be grafted on the nanoparticles of the invention, there may be mentioned:

- sugars and derivatives of sugar such as mannose, which can be grafted onto porous silicon nanoparticles with the aid of a polyethyleneimine or polyethylene glycol PEG linker. Other grafting routes consist of using a phenylsquarate derivative of sugar, such as phenylsquarate-[alpha]-mannose, as illustrated in FIG. 9 and in the experimental part, or a mannose-functionalized ketone as illustrated in FIG. 22B and in the experimental part.
- peptides such as CREKA, iRGD peptides or hormonal target peptides (LH-RH).
- glycodendrimers carrying several monosaccharide or disaccharide derivatives such as mannose, mannose-6-phosphate, glucose, galactose, etc.

The preferred nanoparticles of formula (I) belong to the following list:

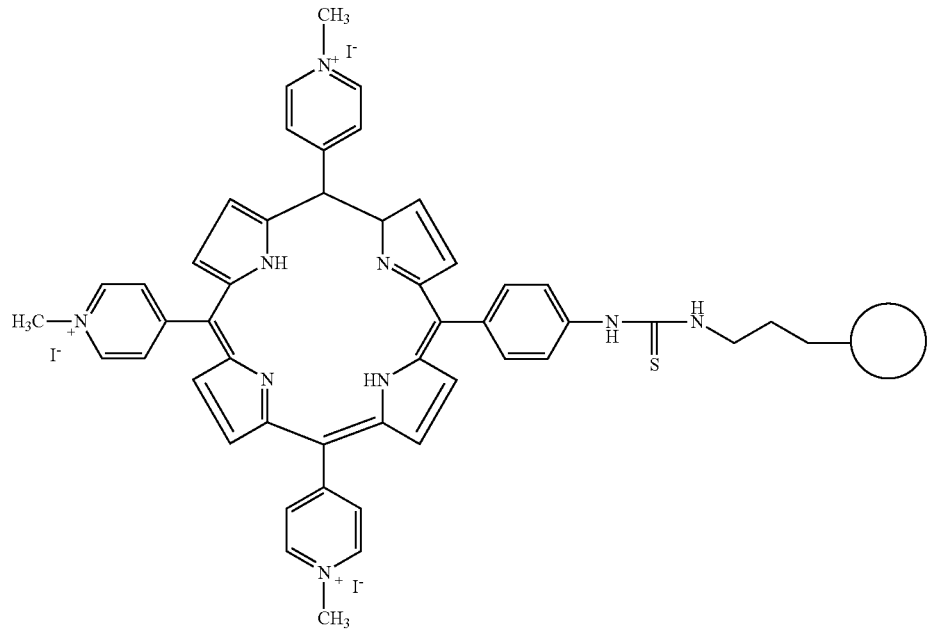

-continued

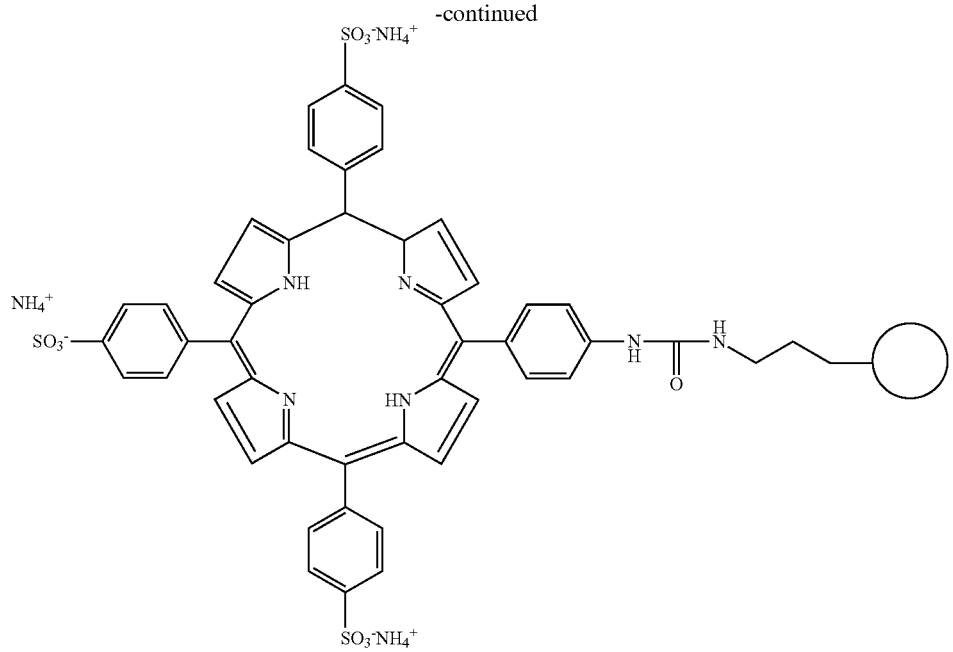

The Production of the Nanoparticles of the Invention:

The nanoparticles of the invention can be produced in particular by a method shown in FIGS. 1, 6, 7, 8, 9, 14A, 20, 22A and 22B.

In a first step, porous silicon nanoparticles are prepared, according to methods known to a person skilled in the art.

These nanoparticles are then functionalized to bear, on their surface, at least one $NH_2$ group or at least one isocyanate, isothiocyanate or semicarbazide group.

The nanoparticles are then grafted with at least one photosensitizing molecule, in particular a porphyrin, using a molecule bearing a group complementary to the one borne by the nanoparticle, so as to form a urea or thiourea bond.

Unlike other covalent bonds, the synthesis of which has been tested on this type of structure, urea and thiourea bonds form under simple synthesis conditions and are preferred over other types of bond between the nanoparticle and the photosensitizing molecule, such as physisorption for example.

The nanoparticles are then advantageously grafted with at least one targeting molecule.

Preparation of the Porous Silicon Nanoparticles:

This step makes use of methods well known to a person skilled in the art. Such methods have been described in particular in WO 2010096733, WO 2009009563 and WO 2006050221, Ji-Ho Park et al., Nature Materials, 8 Apr. 2009, 331-336.

The nanoparticles of the invention are based on silicon.

Silicon is the chemical element with the symbol Si and the atomic number 14. Silicon is occasionally found as a pure free element in nature, but it is more widely present in various silicon dioxide (silica) or silicate forms. Silicon is used in the electronics industry in the form of high-purity silicon to make wafers. Pure silicon is used to produce ultra-pure silicon wafers used in the semiconductor industry, in electronics and in photovoltaic applications. Ultra-pure silicon can be doped with other elements to adjust its electrical response by controlling the number and the charge (positive or negative) of the current carriers. In photonic mode, silicon can be used as a support for a continuous-wave Raman laser to produce a coherent light. The silicon used to carry out the invention is preferably doped. The silicon used to carry out the invention advantageously comprises a positive doping with boron. For example, a doping with boron of about 1 atom in 1000 can be used.

Silicon oxide generally consists of one silicon atom bonded to a single reactive oxygen species (for example a radical). These silicon oxide compounds are useful for adding carbon or other chemical elements in which a bond is formed between the oxygen and the reactive element or a chemical side chain.

Silicon dioxide refers to the compound $SiO_2$ (also called silica). Silicon dioxide is formed when silicon is exposed to oxygen (or air). A thin layer (of approximately 1 nm or 10 A) of native oxide is formed on the surface when silicon is exposed to air under ambient conditions. Higher temperatures and alternative environments are used to produce layers of silicon dioxide on silicon. Silicon dioxide is inert and harmless.

The porous silicon nanoparticles used in the present invention are advantageously prepared by electrochemical etching of monocrystalline silicon wafers in a hydrofluoric acid (HF) ethanol solution followed by detachment of the porous film and treatment by ultrasound according to a procedure shown in FIG. 1 and known to a person skilled in the art (Sailor, M. J. et al., Adv. Funct. Mater. 2009, 19 (20), 3195-3208; Bley, R. A. et al., Chem. Mat. 1996, 8 (8), 1881-1888).

The size of a nanoparticle plays a crucial role in its biocompatibility. For example, particles in the range 20-200 nm tend to have the longest circulation times in the blood (Park, J.-H. et al., Nature Mater. 2009, 8, 331-336; Ruoslahti, E. et al., J. Cell Biol. 2010, 188 (6), 759-768; Lundqvist, M. et al., Nanoparticle size and surface properties determine the protein corona with possible implications for biological impacts. Proceedings of the National Academy of Sciences 2008, 105 (38), 14265; De Jong, W. H. et al., Biomaterials 2008, 29 (12), 1912-1919; Akerman, M. E.

et al., Proc Natl Acad Sci USA 2002, 99 (20), 12617-21; Decuzzi, P. et al., J. Control. Release 2010, 141 (3), 320-327; Park, J.-H. et al. Small 2009, 5 (6), 694-700). The nanoparticles have cell internalization kinetics that depend on their size, (Win, K. Y. et al., Biomaterials 2005, 26 (15), 2713-2722) and a cytotoxicity that depends on their size has been observed for concentrations of formulations of nanoparticles with equivalent mass (Choi, J. et al., J. App. Tox. 2009, 29 (1), 52-60)). Moreover, the degradation rate of a nanoparticle often depends on the diameter of the particles, which in turn affects the medicament-release profile of a therapeutic nanoparticle.

Porous Si is a product resulting from the electrochemical treatment of simple crystalline Si plates in a hydrofluoric acid electrolyte solution. The morphology of the pores and the size of the pores can be modified by controlling the current density, the type and concentration of dopant, the crystalline orientation of the Si plate, and the electrolyte concentration. The type of dopant in the original silicon plate is important because it determines the availability of the valency band of the holes.

In general, the characteristics of the dopant can be divided into four groups based on the type and concentration of the dopant: n-type, p-type, heavily doped n-type, and heavily doped p-type. By heavily doped is meant the levels of dopant at which the conductivity behaviour of the material is more metallic than semiconductive. The application of an anodic current oxidizes a surface silicon atom, which is then attacked by fluorine. The formation of pores occurs when Si atoms are eliminated in the form of $SiF_4$, which reacts with two equivalents of $F^-$ in solution to form $SiF_6^{2-}$. The porosity of a porous Si layer is proportional to the current density applied, and it is typically comprised between 40 and 80%. The pores form at the porous Si/Si interface and, once formed, the morphology of the pores does not change significantly for the remainder of the etching process. However, the porosity of a growing layer can be modified by changing the applied current. The film will continue to grow with this new porosity.

This property makes it possible to construct nanostructures in layers simply by modulating the current applied over the course of an electrochemical etching.

The ability to easily control the size of the pores and pore volumes by adjusting the current parameters during the etching is a unique property of porous Si which is very useful for applications in the administration of medicaments.

Functionalization of the Surface of the Nanoparticles:

Surface chemistry plays an important part in the grafting of the nanoparticles and the control of the degradation properties of porous Si in vivo. After an electrochemical etching treatment, the surface of the Si nanoparticles is covered with reactive species of the hydride type. These chemical functionalities provide a starting point for various reactions which determine the rates of dissolution in aqueous medium, make it possible to fix the photosensitizing molecules and targeting molecules, and control the medicament-release rates.

The two most important modification reactions are the chemical oxidation and the grafting of Si—C species.

Modification of the Surface of the Porous Silicon Nanoparticles:

First of all, the porous silicon nanoparticles are chemically modified with the aid of functional ligands.

Hydrophilic porphyrin-type synthetic molecules are covalently grafted to the porous silicon nanoparticles functionalized by these ligands with the aid of novel chemical reactions. Advantageously, targeting agents are also fixed to the porous silicon nanoparticles.

The chemical modification of the porous silicon nanoparticles by functional ligands:

The freshly etched porous silicon nanoparticles contain Si—H bonds on their surface and are very hydrophobic. Two main surface modifications have been studied.

Controlled oxidation (thermal oxidation, oxidation by ozone, dimethyl sulphoxide, or aqueous borate) followed by silanization: Si—OH groups and $SiO_2$ species are produced on the surface of the porous silicon nanoparticles. These groups make it possible to make the surfaces hydrophilic and biocompatible. As shown in FIG. 6A, a porous silicon particle treated by oxidation has a surface layer of $SiO_2$ which makes it possible, by treatment with a silanizing agent such as aminopropyltriethoxysilane, to graft an aminopropylsilanyl group to the surface of the nanoparticle by a covalent bond. More generally, this type of reaction makes it possible to fix aminoalkylsilanyl groups on the surface of the porous silicon nanoparticles with a W group of variable size.

Hydrosilylation:

Functional groups are fixed to the Si—H terminated surface of porous silicon nanoparticles via Si—C bonds according to the procedure taught in the publication Buriak, J. M., Chem. Rev. 2002, 102 (5), 1272-1308. Hydrosilylation is known to improve the chemical stability of porous silicon-type structures in aqueous media. Isocyanate, amino or semicarbazide functional groups are attached by hydrosilylation with allylamine, allyl isocyanate derivatives, or semicarbazide derivatives (protected or not) as shown in FIG. 6B, and in FIG. 22A. Analogously, it is possible, with the aid of an alkenylamine or an alkenyl isocyanate, to functionalize porous silicon nanoparticles with a W group of variable size.

A functionalized porous silicon is thus obtained

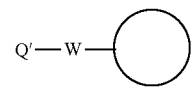

W has the same definition as in formula (I) and Q' represents a group chosen from: —$NH_2$, —N=C=O, —N=C=S, —NH—CO—NH—$NH_2$.

Grafting of the Nanoparticles with a Porphyrin-Type Photosensitizing Molecule.

Porphyrins functionalized by an amino, isocyanate or isothiocyanate group corresponding to formula (II) below are used, in which the parameters x, M, X, R', R", $Z^+$, $Y^-$, $A^-$, R1 have the same definition as in formula (I), Q represents a group chosen from: —$NH_2$, —N=C=O, —N=C=S.

Such molecules are described in particular with their preparation method in J. M. Sutton et al., Bioconjugate chem. 2002, 13, 249-263; Yihui Chen et al., Bioconjugate chem. 2008, 19, 5-9.

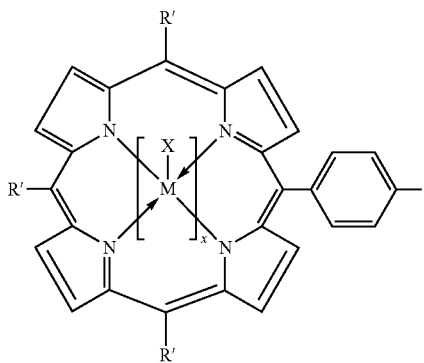

(II)

The synthesis of porphyrins bearing pyridine groups is described in particular in EP-345171 and in WO2010/029232.

When the nanoparticle is grafted with amino groups, a porphyrin grafted with isocyanates or isothiocyanates is used. When the nanoparticle is grafted with isocyanate or isothiocyanate groups, a porphyrin grafted with amines is used. The grafting of the nanoparticles with porphyrin is carried out by formation of a urea or thiourea group.

Grafting of the Nanoparticles with a Targeting Molecule.

The targeting molecules are fixed according to several procedures shown in FIG. 9 that have already been described for mesoporous silica nanoparticles (Brevet, D. et al., Chem. Commun. 2009, 12, 1475-1477; Agemy, L., et al., Blood 2010, 116, 2847-2856), and in FIG. 22B.

The nanoparticles of the invention are preferably grafted on their surface with specific targeting molecules for neoplastic tissues, i.e. biomolecules the receptors of which are overexpressed by cancer cells, or on the surface of cancer cells. These targeting molecules make it easier to transfer the nanoparticles to their biological target. In general, these targeting molecules can be chosen from: folic acid, peptides, carbohydrates, antibodies. They can be grafted onto the nanoparticles of the invention via a polymeric linker.

If the formulations have reduced circulation properties, PEG chains can be used to connect the nanoparticles to the glucidic fraction by coupling with the aid of squarate and amide or semicarbazone functionalities. Chitosan or serum albumin can be used to modify the surface chemistry of the nanoparticles in order to improve their biocompatibility. The molecular weight and chain length of these species can be modulated to optimize the biocompatibility and the cell penetration, and to control the degradation kinetics of the porous silicon nanostructures.

The peptides and/or the targeting agents for cancer cells can be grafted onto the surface of the porous silicon nanoparticles using similar methods. Targeting peptides can be conjugated to modified nanoparticles based on porous silicon via the cysteine sulphhydryl group using an allyl group with a PEG-MAL bond which can be added to the already modified surface of the porous Si nanoparticle by means of hydrosilylation.

According to a variant of the invention, the targeting molecules and the porphyrin are grafted in the course of a single step.

The Uses of the Nanoparticles of the Invention:

The nanoparticles of the invention can be used for therapeutic and/or diagnostic purposes.

The production of singlet oxygen and therefore destruction of the cancer cells is induced by photonic excitation: After irradiation of the nanoparticles with a light source emitting in the infrared in monophotonic or biphotonic mode, the singlet oxygen formed makes it possible to destroy the tumour cells, as shown in FIGS. 19, 31 and 32. The irradiation is carried out at a wavelength comprised between 650 nm and 900 nm. In biphotonic mode, the irradiation is preferably carried out for three to twelve scans of 1.57 s each at a power of 20 to 140 mW, advantageously 50 to 100 mW, and better still at about 80 mW and for a scanned surface area of 1.5×1.5 mm$^2$, i.e. a fluence of 10.6 J cm$^{-2}$ to 42.4 J cm$^{-2}$. In monophotonic mode, the irradiation is preferably carried out by irradiation for 40 min at a power of 7 mW, i.e. a fluence of 16.8 J/cm$^2$.

In particular, the biphotonic irradiation of luminescent porous silicon in the infrared followed by the transfer of energy from the porous silicon to the photosensitizing molecules allows an effective treatment of the target cells, by an activation mechanism of the photosensitizing molecules different from the one carried out by a monophotonic irradiation and having treatment possibilities that are less invasive for the patient, with fewer side effects than the treatments of the prior art.

Moreover, because of the luminescent properties of the porous silicon and the fluorescence of the porphyrin, these nanoparticles allow the visualization of the targeted tumour tissues by luminescence and therefore a monitoring of the efficacy of the treatment, as shown in FIGS. 18, 29, 30A and 30B. Moreover, the porphyrins incorporated in the nanoparticles (I) are fluorescent if the metal cations M are diamagnetic or if x=0, and the nanoparticles of the invention also make it possible, by this means, to carry out fluorescent labelling of the zones where the cancer tissues are located. Certain molecules of formula (I) comprise a paramagnetic metal cation (M in porphyrin) which makes it possible to monitor the distribution of the nanoparticles in the organism by NMR and IRJVI. These properties are just as useful for detecting a pathology as for monitoring the treatment thereof.

The results obtained show that the synthesized nanoparticles are effective for generating singlet oxygen in solution, but with a low quantum yield (FIGS. 17, 23 and 24). These nanoparticles must allow a vectorization of the active ingredients and the endocytosis thereof in the tumour cells after surface functionalization by biomolecules.

Among the different cancers that it is possible to envisage treating with the nanoparticles of the invention, there may be mentioned: retinoblastoma (cell lines Y-79), colon cancer (cell lines HT29), skin cancer (A 431), lung cancer (A 549), breast cancer (MDA-MB-231, MCF-7), cervical cancer (HeLa), ovarian cancer (PEO 14), melanoma (MDA-MB-435), prostate cancer (LNCaP) as well as all solid tumours, which includes but is not limited to head and neck cancers, cancers of the digestive system and of the sexual organs, and any benign or cancerous tumour that can be illuminated. As infrared radiation penetrates better into the organism than visible radiation, the nanoparticles of the invention make it possible to effectively reach cancerous tissues that cannot be accessed by the treatments of the prior art.

After endocytosis the cell lines are irradiated, and the effectiveness of the nanoparticles is evaluated by an MTT assay.

The nanoparticle compositions of the invention can be administered locally or by systemic route. Local administration can be carried out in particular by injection of the nanoparticle composition close to the tumour zone. In the case of the superficial tumours, the nanoparticle compositions can be administered by topical route, in a suitable dosage form (solution, suspension, paste, patch). Administration by general route can be carried out by intravenous, intramuscular, subcutaneous, intraperitoneal or rectal route. Such formulations and the manner of their use are well known to a person skilled in the art. The dosage of active ingredient of formula (I) or (Ia) in the composition is adapted as a function of the weight and age of the patient, the nature, location and development stage of the tumour, the chosen administration route and the irradiation dose used.

The composition can comprise any other active ingredient known for the treatment of tumours and/or their symptoms. It comprises the conventional pharmaceutical components adapted to the chosen method of administration. In particular, it can be in a pharmaceutical form that promotes vectorization to the target tissues.

The nanoparticles of the invention allow the treatment of various diseases including cancers, tumours, cell proliferation diseases, inflammatory diseases and tissue lesions. They can be used in particular for the treatment of skin diseases.

The nanoparticles of the invention can be combined with a cosmetically acceptable support to form a cosmetic composition. In particular, they can be formulated in the form of a skincare cream, cosmetic patch, mask.

These nanoparticles can be used to treat, prevent, delay the appearance and/or recurrence of a pathology chosen from cancers, tumours, cell proliferation diseases. They also make it possible to detect these pathologies.

Another subject of the invention is a kit for the detection, treatment, prevention, delay of the appearance and/or recurrence of a pathology chosen from cancers, tumours, cell proliferation diseases, comprising:
porous silicon nanoparticles grafted covalently with at least one photosensitizing molecule, or a medicinal composition comprising them
and
means that allow a biphotonic irradiation in the infrared.

Among the means that can be used for the irradiation in the infrared in biphotonic mode, there may be mentioned a focused titanium-sapphire femtosecond laser.

In fact, the inventors have demonstrated for the first time the ability of porous silicon nanoparticles, grafted covalently with at least one photosensitizing molecule, to form oxidizing species capable of destroying malignant cells under the effect of a biphotonic irradiation in the near infrared.

According to this variant, the photosensitizing molecules can be of any type, since they are grafted via a covalent bond to the porous silicon nanoparticles. In particular, they can be chosen from porphyrins, but also from chlorins or bacteriochlorins. According to this variant, the porous silicon nanoparticles are preferably also grafted with at least one targeting molecule that makes it possible to target neoplastic tissues specifically.

Another subject of the invention is a method for treating, preventing, delaying the appearance and/or recurrence of a pathology chosen from cancers, tumours, cell proliferation diseases, comprising: administering to an individual to be treated porous silicon nanoparticles grafted via a covalent bond with at least one photosensitizing molecule and treatment by biphotonic irradiation in the near infrared.

Another subject of the invention is a kit for the treatment, prevention and/or detection of a pathology chosen from cancers, tumours, cell proliferation diseases, comprising nanoparticles of formula (I) or (Ia) or pharmaceutical compositions comprising them and means that allow an irradiation in the infrared, in particular biphotonic irradiation means.

FIGURES

FIG. 1: Diagrammatic representation of the preparation of silicon nanoparticles by electrochemical anodization of crystalline silicon, electrodissolution, and ultrasonic fracturing.

FIG. 2: SEM imaging photograph of a porous silicon film, precursor of the nanoparticles, on the surface (2A) and in cross section (2B).

FIG. 3: SEM (3A) and TEM (3B) imaging photograph of the porous silicon nanoparticles prepared by ultrasonic fracturing and shown in FIG. 1.

FIG. 4: Graph showing the light scattering intensity in kcps as a function of the size of the nanoparticles (hydrodynamic diameter measured in nm).

FIG. 5: Graph showing the nitrogen adsorption and desorption isotherm for the porous silicon nanoparticles etched at 200 mA/cm$^2$. The adsorbed quantity (volume adsorbed in mL STP/g) is shown as a function of the relative pressure $P/P_0$.

FIG. 6: Diagrammatic representation of two synthesis routes that make it possible to graft functional groups onto porous silicon nanoparticles.

FIG. 7: Diagrammatic representation of the coupling of an amine porphyrin on a porous silicon nanoparticle functionalized by an allyl isocyanate group.

FIG. 8: Diagrammatic representation of the coupling of a porphyrin functionalized by an isocyanate on a porous silicon nanoparticle functionalized by an allylamine group.

FIG. 9: Diagrammatic representation of the coupling of a mannose group on a porous silicon nanoparticle via a squarate group.

FIG. 10A: Graph showing the FTIR spectrum (wavenumber in cm$^{-1}$) of the porous silicon nanoparticles not grafted (solid) and hydrosilylated with allylamine (dotted). FIG. 10B: Graph showing the FTIR spectrum (wavenumber in cm$^{-1}$) of porous silicon nanoparticles at different stages of the coupling of a mannose-squarate: after hydrosilylation by an allylamine (solid), after coupling with mannose (dotted).

FIG. 11: Graph showing the UV-VIS spectrum of a solution obtained after dissolution, in KOH, of the porous silicon nanoparticles grafted with porphyrin-NCS, with 74 µg porphyrin/mg nanoparticles, i.e. a loading of 7.4% by mass (absorbance Log I/I0 as a function of the wavelength in nm).

FIG. 12: Graph showing the FTIR spectrum (wavenumber in cm$^{-1}$) of porous silicon nanoparticles at different stages of the coupling of a porphyrin-NCS: after hydrosilylation by an allylamine (solid), after coupling with porphyrin-NCS (dotted).

FIG. 13: Graph showing the FTIR spectrum (wavenumber in cm$^{-1}$) of porous silicon nanoparticles grafted with a porphyrin-NH$_2$ by the allyl isocyanate route.

FIG. 14A: Graph showing the FTIR spectrum (wavenumber in cm$^{-1}$) of porous silicon nanoparticles at different stages of the simultaneous coupling of a mannose-ketone and a porphyrin-NCS: (a) porous silicon grafted with semicarbazide, (b) after hydrosilylation by an allylamine, (c) after coupling with porphyrin-NCS.

FIG. 14B: Graph showing the UV-VIS spectrum of a solution obtained after dissolution, in KOH, of the porous silicon nanoparticles grafted with porphyrin-NCS and with semicarbazide, with 10 µg porphyrin/mg nanoparticles (absorbance Log I/I0 as a function of the wavelength in nm).

FIG. 15: Graph showing the produced quantity of singlet oxygen as a function of the wavelength of irradiation for nanoparticles without porphyrin (intensity expressed in arbitrary units: phosphorescence of the singlet oxygen as a function of the wavelength in nm).

FIG. 16: Graph showing the UV-VIS spectrum of the porous silicon nanoparticles grafted with a porphyrin and with mannose (absorbance in Log I/I0 as a function of the wavelength in nm).

FIG. 17: Graph showing the produced quantity of singlet oxygen as a function of the wavelength of irradiation for porous silicon nanoparticles grafted with a porphyrin and with mannose (intensity expressed in arbitrary units: phosphorescence of the singlet oxygen as a function of the wavelength in nm).

FIG. 18: Confocal microscopy images of living MCF-7 breast cancer cells. The cells were incubated for 5 h with 20 pg ml−1-pSiNP Porph-NH$_2$ nanoparticles, 0.25 µg ml−1 Porph-NH$_2$, or a vehicle (ethanol) and co-coloured with a membrane marker (cell mask). The cell membranes were visualized in green at 561 nm, the nanoparticles and the porphyrins were visualized at 633 nm and the images have been merged. The photos represent at least 3 independent experiments. The intracellular aggregates of pSiNP-Porph-NH$_2$ are identified by "solid" arrows and the aggregates of the cell membrane, which look yellow in the merged image, are labelled with "dotted arrows". The scale bars are at 5 µm.

Left-hand column: membrane, middle column: compounds, right-hand column: merged.

First row: control, second row: porphyrin-NH$_2$, third row: porous silicon nanoparticles grafted with porphyrin-NH$_2$.

FIG. 19: Graph showing the % of living MCF7 cells as a function of the treatment which has been administered to them. Efficacy of the in vitro PDT in biphotonic excitation mode on the MCF-7 cells incubated with: control culture medium containing 4% ethanol (EtOH, control experiment), free porphyrin-NCS (porph-NCS), non-grafted porous silicon nanoparticles (Si), porous silicon nanoparticles grafted with mannose (Si-m), porous silicon nanoparticles grafted with porphyrin-NCS (Si-p) and porous silicon nanoparticles grafted with porphyrin and with mannose (Si-m-p). Irradiation at 750 nm, 3 scans of 1.57 s. The living cells are counted by an MTS assay 2 days after irradiation.

FIG. 20: Diagrammatic representation of the preparation of the nanoparticles grafted with a porphyrin.

FIG. 21: X-ray diffractograms of the porous silicon nanoparticles: FIG. 21A at wide angles, FIG. 21B at narrow angles. The relative intensity (u.a.) is shown as a function of 2θ (in degrees)

FIG. 22A: Diagrammatic representation of the coupling of a semicarbazide group on a porous silicon nanoparticle by hydrosilylation.

FIG. 22B: Diagrammatic representation of the coupling of a mannose group on a porous silicon nanoparticle via a semicarbazone function.

FIG. 23: Curves plotting ln(A) as a function of the illumination time (minutes) for methylene blue (diamond), porphyrin-NCS (triangle) and porous silicon nanoparticles grafted with porphyrin-NCS (square).

FIG. 24: Curves plotting the absorbance at 411 nm ln(A) as a function of the illumination time (minutes) for DPBF on its own (square), and for porous silicon nanoparticles grafted with porphyrin-NH$_2$+DPBF (diamond).

FIG. 25: Kinetics of the release of porphyrin-NCS from the porous silicon nanoparticles grafted with porphyrin-NCS incubated at 37° C. in different media. Diamond: in PBS at pH=7.4, square: in DMEM culture medium with 10% FBS, triangle: in DMEM culture medium without serum.

FIG. 26: Release kinetics of the porphyrin-NH$_2$ from the nanoparticles grafted with porphyrin-NH$_2$, incubated at 37° C. in PBS (pH=7.4). The stability of the porous silicon nanoparticles grafted with porphyrin-NH$_2$ in PBS was monitored by spectroscopic determination of the quantity of porphyrin occurring in the solution as a function of the time (hours). The data show that 50% of the porphyrin was released at the end of 5 h, and that 89% of the porphyrin was released after 48 h of incubation. Under the experiment conditions used in this study, this degradation time is compatible with the use of the porous silicon nanoparticles grafted with porphyrin-NH$_2$ for imaging and PDT.

FIG. 27: Quantification of the porphyrin-NH$_2$ contained in the porous silicon nanoparticles (black) and of the free porphyrin (grey) internalized in the living MCF-7 breast cancer cells after 5 h of incubation. The internalization was monitored by a spectroscopic determination of the quantity of porphyrin in the cell lysates and compared with a series of dilutions. The quantity of porphyrin internalized from the nanoparticles is in the range 105±5 ng·ml−1 porphyrins, whereas the free porphyrin internalized corresponds to 35±5 ng·ml−1.

FIG. 28: Semi-quantitative analysis of nanoparticles grafted with porphyrin-NH$_2$ (pSiNP-Porph-NH$_2$) and of the free porphyrin (Porph-NH$_2$) internalized in the living MCF-7 breast cancer cells after 5 h of incubation. An average intensity inside the cells was determined from five distinct zones and expressed as greyness per µm$^2$. It was noted that the internalized nanoparticles represent 45% of the total of the nanoparticles detected.

FIG. 29: Confocal microscopy images, in monophotonic excitation mode at 405 nm, of MCF-7 cells incubated with control medium, of non-grafted pSiNP (porous silicon nanoparticles), of free porphyrin-NCS, of pSiNP-porphyrin-NCS and of pSiNP-mannose-porphyrin-NCS. On the left: autofluorescence of the cells (emission collected between 540 nm and 620 nm), in the middle: nanoparticles and porphyrin (emission collected between 620 nm and 700 nm), on the right: superimposition of two fluorescence images. a) control, b) pSiNP c) free porphyrin-NCS d) pSiNP-porphyrin-NCS e) pSiNP-mannose-porphyrin-NCS.

FIGS. 30A and 30B: Multiphoton confocal microscopy imaging of MCF-7 cells incubated with the different types of porous silicon nanoparticles. The images were taken with a spectral detector during a biphotonic excitation at 750 nm. On the left: fluorescence of the membrane marker (Cell Mask Orange), in the middle: fluorescence emitted between 620 and 700 nm, on the right: superimposition of the two fluorescence images. a) ethanol b) pSiNP (porous silicon nanoparticles) c) free porphyrin-NCS d) pSiNP+free porphyrin e) pSiNP-porphyrin-NCS f) pSiNP-mannose g) pSiNP-mannose+free mannose h) pSiNP-mannose-porphyrin-NCS i) pSiNP-mannose-porphyrin-NCS+free mannose.

FIG. 31. Efficacy of the in vitro PDT in monophotonic excitation mode, as a percentage of living cells, with free porphyrin-NH$_2$ at 0.25 µg/mL, non-grafted pSiNP (porous silicon nanoparticles) at 20 µg/mL and pSiNP-porphyrin-NH$_2$ at 20 µg/mL, with or without irradiation. Irradiation at 650 nm (14 J/cm$^2$) for 40 min. The living cells are counted by an MTT assay 2 days after irradiation.

FIG. 32. Efficacy of the in vitro PDT in monophotonic excitation mode, as a percentage of living cells, on the MCF-7 cells incubated with: control culture medium containing 4% ethanol (EtOH, control experiment), free porphyrin-NCS (porph-NCS), non-grafted porous silicon nanoparticles (Si), porous silicon nanoparticles grafted with mannose (Si-m), porous silicon nanoparticles grafted with porphyrin-NCS (Si-p) and porous silicon nanoparticles grafted with porphyrin and with mannose (Si-m-p). Irradiation at 650 nm, 7 mW/cm$^2$, 40 min. The living cells are counted by an MTS assay 2 days after irradiation.

FIG. 33. Dotted: normalized UV-VIS absorption spectrum of the porphyrin-NCS. Solid: normalized emission spectrum of the porous silicon nanoparticles in water (excitation at 250 nm).

EXPERIMENTAL PART

1. Synthesis of the Biodegradable Porous Silicon Nanoparticles and Chemical Functionalization This part describes the preparation of the nanostructured components/nanoparticles and the development of novel grafting chemistries for attaching porphyrins and targeting agents, in order to study their effectiveness in targeting, penetrating and delivering the porphyrin-type therapeutic agents to in vivo cancer or endothelial cells.

1.1. Synthesis and Characterization of the Porous Silicon Nanostructures/Nanoparticles The porous silicon nanoparticles are prepared by electrochemical etching of monocrystalline silicon wafers in a hydrofluoric acid (HF) electrolyte solution in ethanol, followed by detachment of the porous layer by electrodissolution and an ultrasonic fracturing in accordance with a published procedure (FIG. 1), (Sailor, M. J. et al., Adv. Funct. Mater. 2009, 19 (20), 3195-3208; Bley, R. A. et al. Chem. Mat. 1996, 8 (8), 1881-1888).

Monocrystalline silicon of the p++ type (doped with boron, resistivity 0.8-1.2 mΩ·cm, orientation, <100>) is etched electrochemically in a solution of hydrofluoric acid (48%)/ethanol at 3:1 by volume (FIG. 1, first step). The etching is carried out in a Teflon cell, using a circular platinum counter electrode. A constant current of 200 mA/cm$^2$ is applied for 150 seconds, and the sample is rinsed three times with ethanol. The porous layer is then electrodissolved in a solution of HF in ethanol at 3.3% by applying a constant current of 4 mA/cm for 250 seconds (step 2 of FIG. 1). After rinsing three times with ethanol, the porous layer is deposited in ethanol, in a glass flask. After having been degassed under a nitrogen flow for 20 minutes, the sample is sonicated in an ultrasonic bath for 16 hours (steps 3 and 4 of FIG. 1). The obtained dispersion of particles in ethanol is filtered (0.2-μm nylon syringe filter) and centrifuged at 14000 rpm for 30 minutes. Nanoparticles with a size distribution centred on 115 nm are obtained (FIG. 4). The size and the texture of the nanoparticles are characterized by scanning electron microscopy (SEM), transmission electron microscopy (TEM), light scattering (DLS) and nitrogen adsorption (BET). The nanoparticles are also characterized by X-ray diffraction.

1.2. Modification of the Surface of the Porous Silicon Nanostructures/Nanoparticles Hydrophilic synthetic porphyrins are anchored covalently onto the surface of the porous silicon nanostructures/nanoparticles by novel grafting chemistries. Targeting species are also grafted onto the surface of the porous silicon nanostructures/nanoparticles. Upstream of the grafting of the targeting species and the porphyrins, the porous silicon nanostructures/nanoparticles are chemically modified by functional ligands.

1.2.1. Chemical Modification of the Porous Silicon Nanostructures/Nanoparticles by Functional Ligands:

The freshly etched porous silicon nanostructures/nanoparticles, having Si—H bonds on their surface, are very hydrophobic. Two surface modifications are developed.

Figure 1:
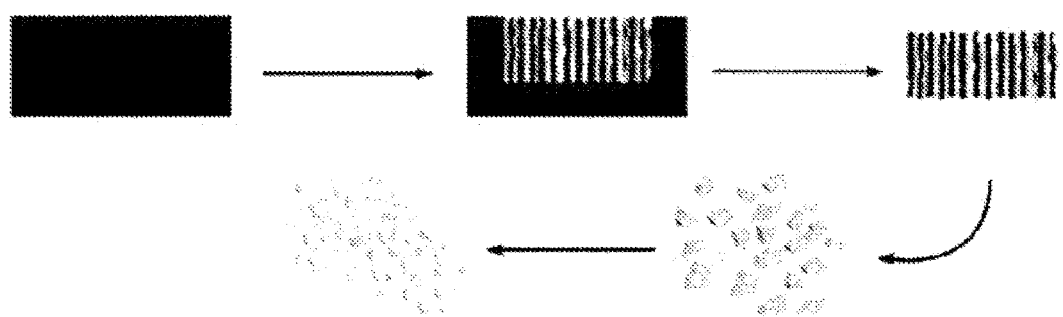
Figure 2:
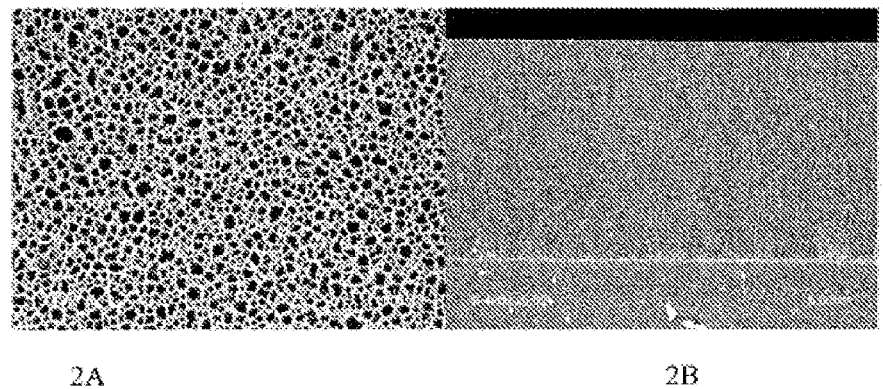
FIG. 2 shows the SEM image of a surface and of a cross section of a porous Si film.
Figure 3:
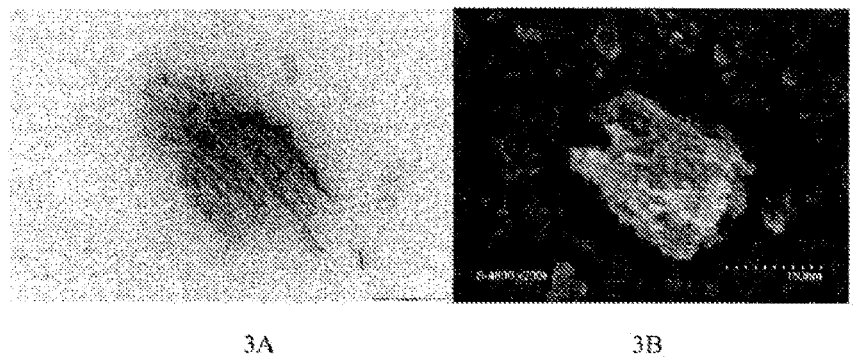
FIG. 3 shows the SEM and TEM images of porous Si nanoparticles prepared by ultrasonic fracturing of the porous film shown in FIG. 2.
Figure 4:
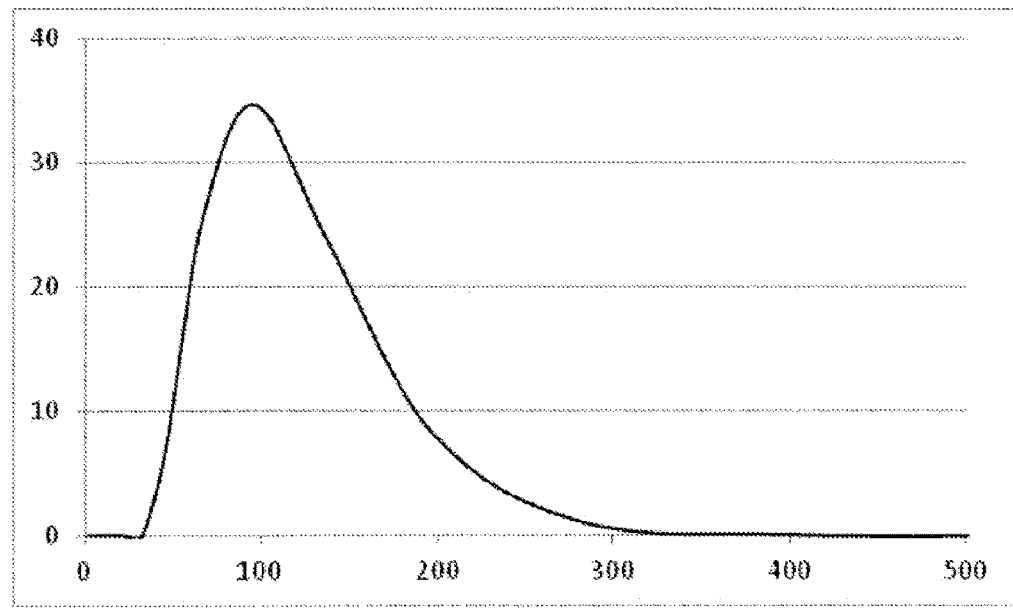
FIG. 4 shows the light scattering curve for the porous Si nanoparticles shown in FIG. 3.
Figure 5:
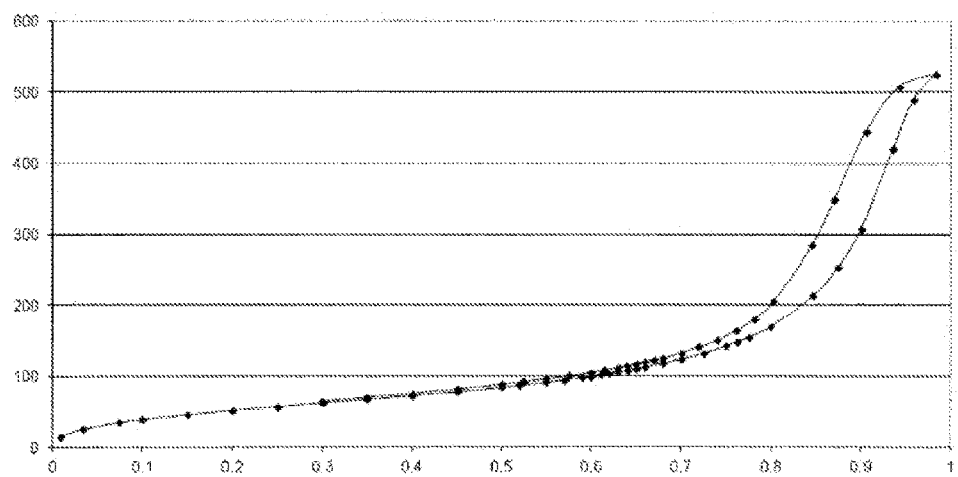
FIG. 5 shows the nitrogen adsorption/desorption isotherm curve for the porous Si nanoparticles shown in FIG. 3.
Figure 6:
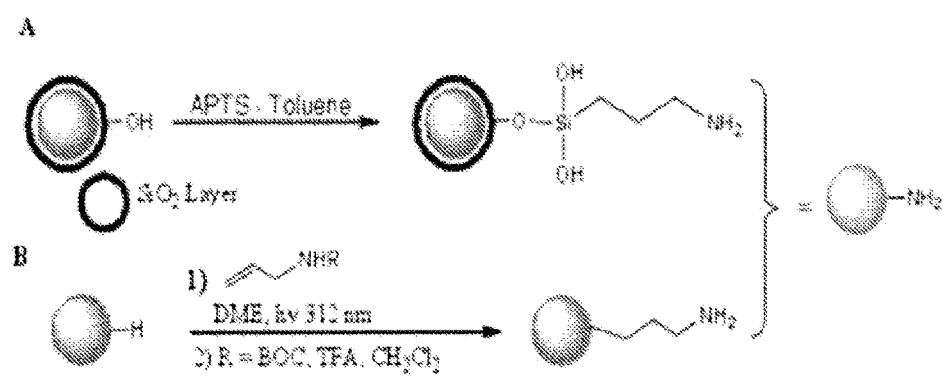

1.2.1.1. Controlled Oxidation (Thermal, by Ozone, Dimethyl Sulphoxide, Aqueous Borate) and Silanization:

Si—OH and SiO$_2$ species are produced on the surface of the nanostructures/nanoparticles. The chemistry of silanization on oxidized surfaces of porous silicon nanostructures/nanoparticles has been developed for the grafting of functional carbon chains such as aminopropyltriethoxysilane, incorporating amine groups (as shown in FIG. 6A), then used for the grafting of porphyrins and targeting species.

After oxidation of the nanoparticles, they are redispersed in aminopropyltriethoxysilane. The silanization reaction is carried out at 150° C. under a nitrogen flow for 2 hours. The nanoparticles are then rinsed 4 times with ethanol and twice with diethyl ether, before being dried under a nitrogen stream.

Figure 22A:
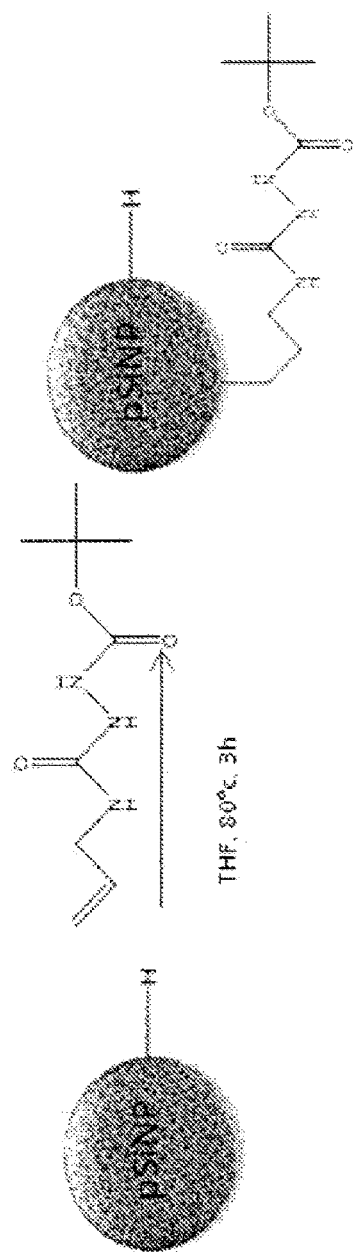

1.2.1.2. Hydrosilylation:

Functional groups are grafted covalently onto the surface of the porous Si nanostructures/nanoparticles via Si—C bonds according to published procedures (Buriak, J. M., Chem. Rev. 2002, 102 (5), 1272-1308). Hydrosilylation is a chemical treatment known to strengthen the chemical stability of porous silicon in aqueous medium (15). Functional groups of the amine, isocyanate and semicarbazide type are anchored by hydrosilylation with allylamine, allyl isocyanate, and allylsemicarbazide derivatives as shown in FIG. 6B and in FIG. 22A.

1.2.2. Grafting of the Porphyrins

Amine and isocyanate porphyrins are grafted onto the different types of ligands (amino and isocyanato) previously anchored to the surface of these porous Si nanoparticles.

1.2.2.1. Grafting of Porphyrin-NH$_2$ onto the Porous Si Nanoparticles Hydrosilylated with Allyl Isocyanate.

The nanoparticles are dispersed in allyl isocyanate. The hydrosilylation is carried out at 90° C. under a nitrogen flow for 3 hours. The particles are then rinsed three times in tetrahydrofuran (THF) and redispersed in 4 ml THF.

500 μL porphyrin-NH$_2$ at 1 mg/mL in dimethylformamide (DMF) is added to 200 μL ethanol. The reaction takes place at 80° C. under nitrogen reflux for 4 hours. The particles are then rinsed twice with ethanol, twice with water, twice with ethanol, and twice with diethyl ether before being dried under a nitrogen stream.

Figure 7:
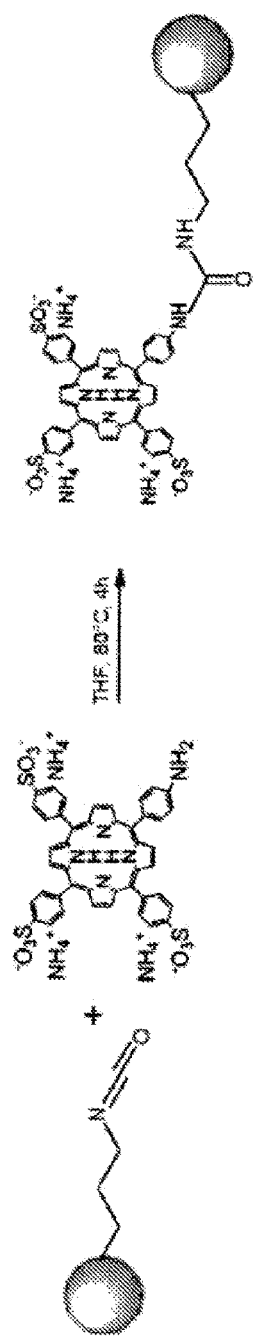

This grafting procedure shown in FIG. 7 has never been described before for porous Si nanoparticles.

Figure 8:
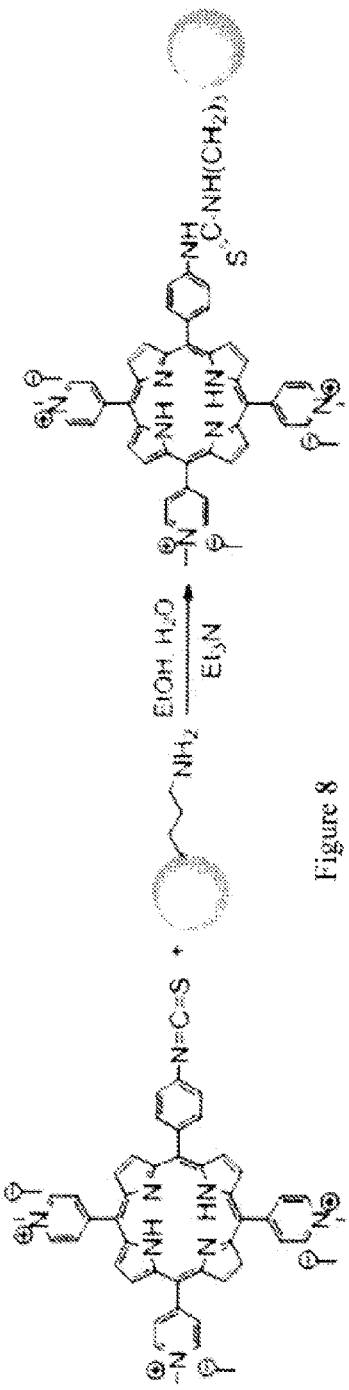

1.2.2.2. Grafting of Porphyrin-NCS onto the Porous Si Nanoparticles Hydrosilylated with Allylamine (Shown in FIG. 8):

The nanoparticles are dispersed in allylamine. This solution is then degassed by three consecutive freeze-pump-thaw cycles.

The hydrosilylation is carried out at 70° C. under a nitrogen flow for 2 hours and the nanoparticles are rinsed four times in ethanol. The particles are redispersed in 2 ml ethanol. 2.5 mL of a solution of H$_2$O/ethanol at 1:1 (by volume) is then added to 500 μL of a solution of porphyrin-NCS at 1 mg/mL in ethanol.

The reaction takes place at ambient temperature accompanied by stirring for 18 hours. The particles are then rinsed four times with ethanol and twice with diethyl ether before being dried under a nitrogen stream.

1.2.3. Anchoring of the Targeting Species

Figure 9:
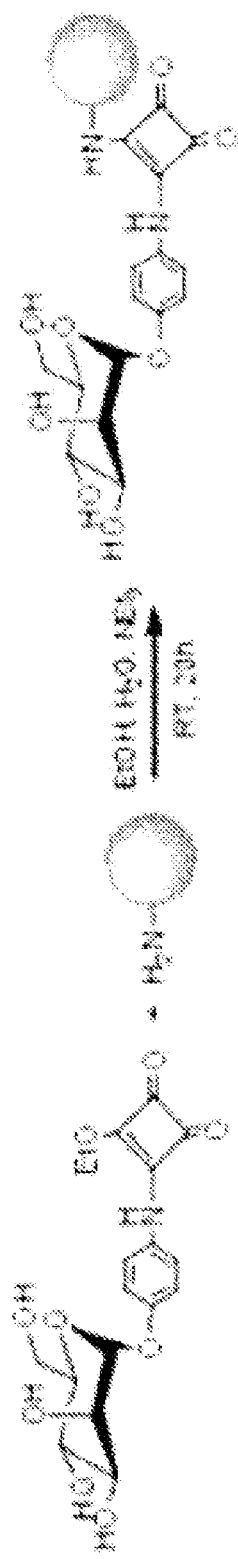
Figure 22B:
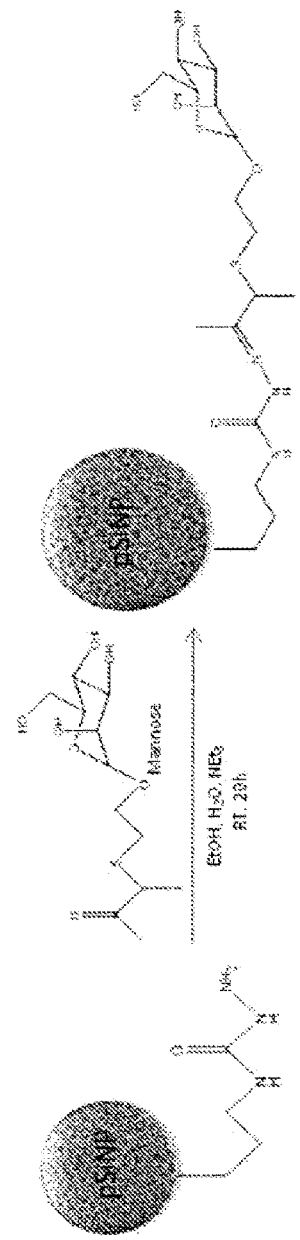

Molecules of the carbohydrate (mannose) type are coupled to the surface of the porous Si nanoparticles according to a procedure developed previously for mesoporous silica nanoparticles and shown in FIG. 9, and according to another procedure shown in FIG. 22B. It has been shown here that squarate and semicarbazide groups allow the coupling of carbohydrate-type molecules under mild conditions. The expected role of the carbohydrate species is the vectorization of the nanoparticles to the cancer cells.

1.2.3.1 Anchoring of a Mannose-Squarate

In a typical reaction, the porous Si nanoparticles are dispersed in allylamine. This suspension is then degassed by three consecutive freeze-pump-thaw cycles.

The hydrosilylation is carried out at 70° C. under nitrogen reflux for 2 hours and the nanoparticles are rinsed four times in ethanol. The particles are redispersed in 2.5 ml ethanol. 2.5 mL of a solution of mannose-squarate at 6 mg/mL in $H_2O$/ethanol at 1:1 (by volume) is then added to 250 µL triethylamine.

The reaction takes place at ambient temperature accompanied by stirring for 18 hours. The nanoparticles are then rinsed four times with diethyl ether before being dried under a nitrogen stream.

1.2.3.2 Anchoring of a Mannose-Ketone

Hydrosilylation of the porous silicon nanoparticles with semicarbazide: The porous silicon nanoparticles dispersed in ethanol are first centrifuged at 22000 g for 30 min, then rinsed twice with THF, with centrifugation at 22000 g for 30 min each time. The nanoparticles are then redispersed in 3 mL of a solution of tert-butyl-2-[(allylamino)carbonyl]hydrazine-carboxylate, at $10^{-1}$ M in THF. The hydrosilylation reaction then takes place at 85° C. for 3 h accompanied by stirring and under a nitrogen flow. The particles are then centrifuged and rinsed twice with THF, once with ethanol and once with dichloromethane.

Deprotection of the Semicarbazide Function

In order to remove the Boc group protecting the semicarbazide function, the porous silicon nanoparticles are centrifuged at 22000 g for 30 min, to then be redispersed in 5 mL of a solution of trifluoroacetic acid (TFA) at 40% by volume in dichloromethane. This dispersion is stirred for 4 h at ambient temperature, then the nanoparticles are rinsed twice with $CH_2Cl_2$, once with ethanol, once with water, once with ethanol and once with $CH_2Cl_2$.

Grafting of Mannose-Ketone

Following the deprotection of the semicarbazide, the nanoparticles are redispersed in 2.5 mL ethanol. 2.5 mL of a solution of mannose-ketone at $1.6 \times 10^{-2}$ M in a 1:1 water/ethanol mixture and 250 µL triethylamine were then added dropwise. The reaction takes place accompanied by stirring and at ambient temperature for 18 h. After the reaction, 4 to 5 washings are carried out with distilled water then two washings with absolute ethanol and two other washings with diethyl ether. Finally, the grafted particles are dried under nitrogen.

1.2.4. Simultaneous Grafting of Mannose-Squarate and of Porphyrin-NCS:

The porous Si nanoparticles are dispersed in allylamine. This suspension is then degassed by three consecutive freeze-pump-thaw cycles. The hydrosilylation is carried out at 70° C. under nitrogen reflux for 2 hours and the nanoparticles are rinsed four times in ethanol. The particles are redispersed in 2 ml ethanol. 2.5 mL of a solution of mannose-squarate at 6 mg/mL in $H_2O$/ethanol at 1:1 (by volume) is then added to 250 µL triethylamine, and to 500 µL of a solution of porphyrin-NCS at 1 mg/mL in ethanol. The reaction takes place at ambient temperature accompanied by stirring for 18 hours. The nanoparticles are then rinsed four times with ethanol and twice with diethyl ether before being dried under a nitrogen stream.

1.2.5. Simultaneous Grafting of a Mannose-Ketone and of Porphyrin-NCS:

Hydrosilylation of the porous silicon nanoparticles with semicarbazide (as above)

Hydrosilylation of the porous silicon nanoparticles with allylamine (as above)

Grafting of porphyrin-NCS (as above)

Grafting of mannose-ketone (as above)

Notes:

1/Galactose can be substituted for mannose, following the same experimental conditions.

2/If the nanoparticle formulations have poor circulation properties, PEG (polyethylene glycol) chains can be used to bond the carbohydrate species to the nanoparticles via squarate or amide couplings.

Chitosan and serum albumin can be used as another alternative surface chemistry for improving the biocompatibility of the nanoparticles. It will be possible to adjust the molecular weight and chain length of the PEGs in order to maximize the biocompatibility, the cell penetration, and in order to control the degradation kinetics of the porous silicon nanostructures.

1.2.6. Characterization

Figure 11:
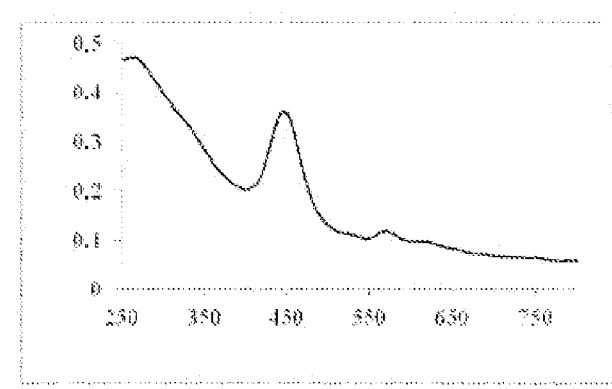
Figure 14A:
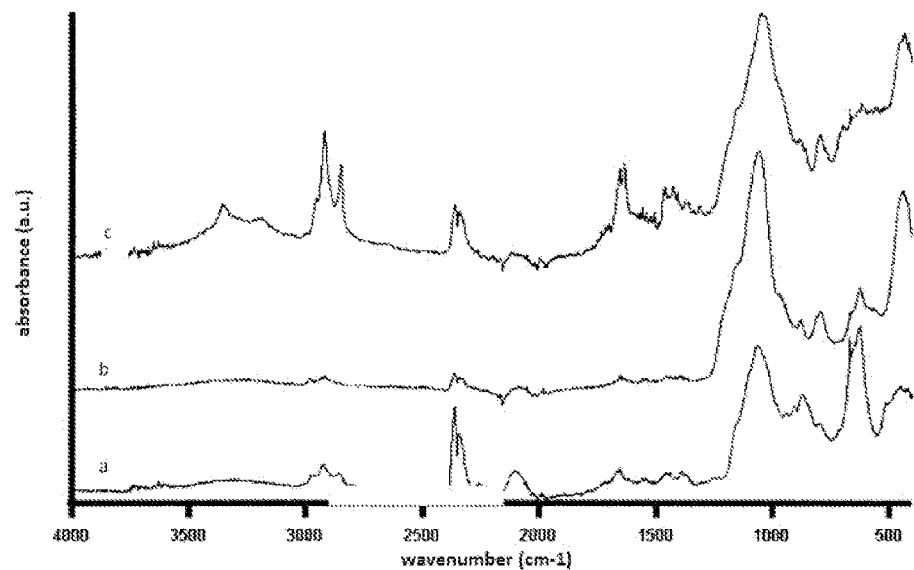
Figure 14B:
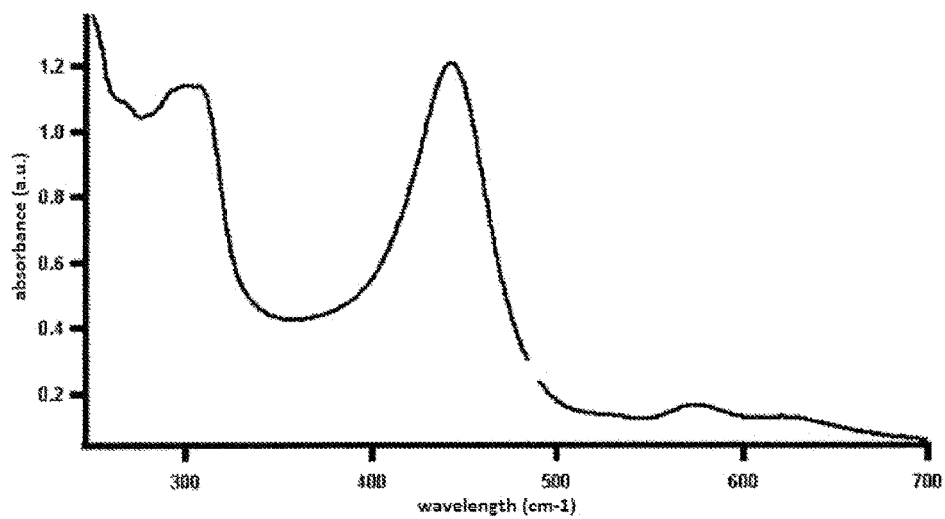

The chemically modified nanoparticles are characterized by infrared vibrational spectroscopy (FTIR), elemental analysis, and XPS for the grafting of the mannose, and by UV-VIS absorption spectroscopy and FTIR for the grafting of the different porphyrins to the surface of the porous Si nanoparticles. For the UV-VIS absorption spectroscopy the porous Si nanoparticles are dissolved in a solution of KOH before the absorbance of porphyrin is measured (FIGS. 11 and 14B).

1.2.6.1. Grafting of Mannose

Figure 10A:
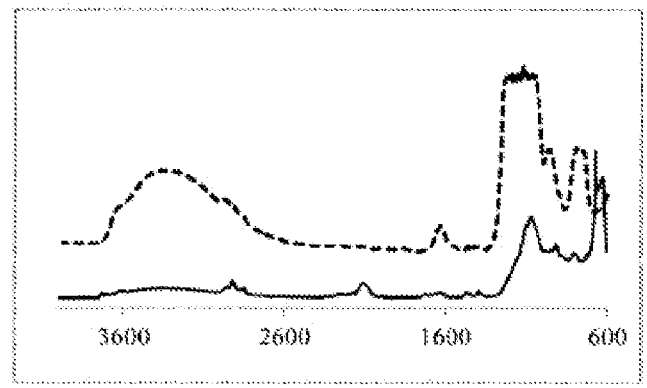
Figure 10B:
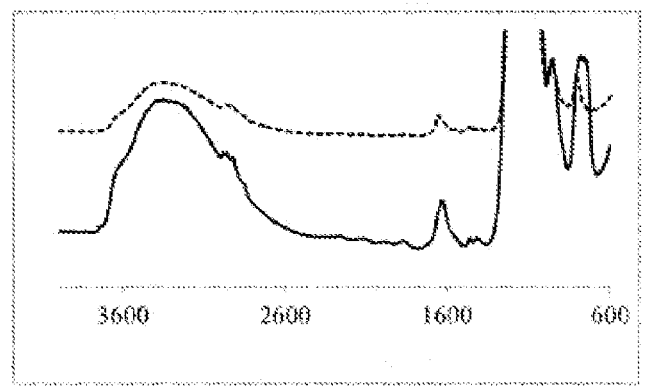

The grafting of mannose-squarate onto the allylamine-functionalized nanoparticles is carried out by nucleophilic addition of the amine followed by the removal of the ethoxy group of the squarate. The electrophilicity of the squarate is increased by the presence of hydrogen bonds with water, a cosolvent of the reaction. The triethylamine catalyzes the reaction by trapping the protons released during the reaction. The FTIR spectrum of the mannose-functionalized nanoparticles is shown in FIG. 10B.

In this FTIR spectrum, the band appearing at 1654 cm$^{-1}$ is attributed to the angular deformation vibration of the N—H bond of the amines that have reacted. The vibration band at 1630 cm$^{-1}$ is always present in the form of a shoulder in the band centred on 1654 cm$^{-1}$. The presence of this band, attributed to the angular deformation of the N—H bond of the primary amine, means that the primary amine is always partially present on the surface of the porous silicon nanoparticles.

The results of the elemental analyses after grafting of the mannose show, below, the percentage of elements present:

5.25% C
0.72% N
4.18% O

These values are consistent with the presence of mannose on the surface of the porous Si particles.

Quantification by XPS

Experimental: The XPS analyses were carried out on a Thermo Electron ESCALAB 250 device from the analysis technical support centre of Montpellier 2 University. The excitation source is the Al Kα line (1486.6 eV). The analyzed surface has a diameter of 400 μm, the photoelectron spectra are calibrated by binding energy relative to the energy of the C—C component of the carbon C1s at 284.8 eV, and the charge is compensated by an electron beam.

TABLE 1

Table showing the quantifications obtained by XPS for the porous silicon nanoparticles grafted with mannose-squarate (on allylamine).

| Name | Peak BE | Height Counts | FWHM eV | Area (P) CPS · eV | Area (N) | At. % |
|---|---|---|---|---|---|---|
| Si2p | 103.22 | 10204.45 | 1.78 | 19956.09 | 0.56 | 30.98 |
| C1s | 284.89 | 3324.17 | 2.73 | 9935.02 | 0.23 | 12.76 |
| N1s | 401.07 | 400.97 | 3.81 | 1551.23 | 0.02 | 1.12 |
| O1s | 532.53 | 65969.95 | 1.62 | 118334.22 | 0.96 | 53.42 |
| F1s | 688.97 | 2728.87 | 1.83 | 5593.67 | 0.03 | 1.72 |

1.2.6.2. Grafting of the Porphyrins

The UV-VIS spectrum of a solution obtained after dissolution, in KOH, of the porous silicon nanoparticles grafted with porphyrin-NCS is shown in FIG. 11. 74 μg porphyrin/mg nanoparticles, i.e. a loading of 7.4% by mass, is obtained.

Figure 12:
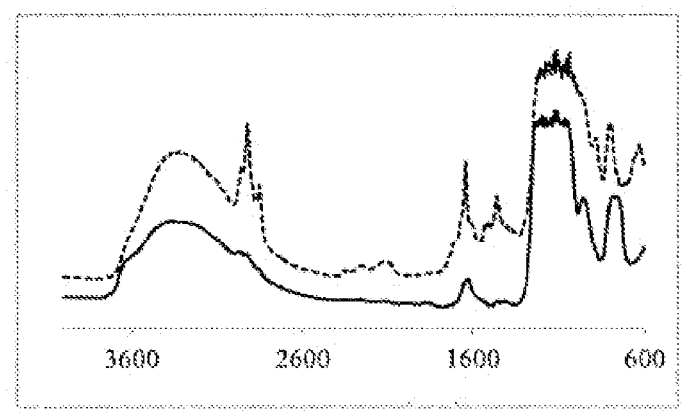

The FTIR spectrum of the porous silicon nanoparticles grafted with a porphyrin-NCS is shown in FIG. 12. Three intense bands are observed between 2850 and 2960 cm$^{-1}$, corresponding to the stretching vibrations of the C—H bonds. This is due to the numerous C—H bonds provided by porphyrin. Between 1460 cm$^{-1}$ and 1600 cm$^{-1}$, the vibrational spectrum is complex. These bands are characteristic of the aromatic C═C bonds present thanks to the porphyrin. The intense band observed at 1642 cm$^{-1}$ could be characteristic of the thiourea bond or of the N—H angular deformation vibration of the amines that have not reacted. Finally, the band observed at 797 cm$^{-1}$ is always attributed to the stretching vibration of the Si—C bond, whereas the bands at 882 cm$^{-1}$ and between 1000 and 1250 cm$^{-1}$ (stretching vibrations of the Si—O bonds) indicate a partially oxidized surface.

Figure 13:
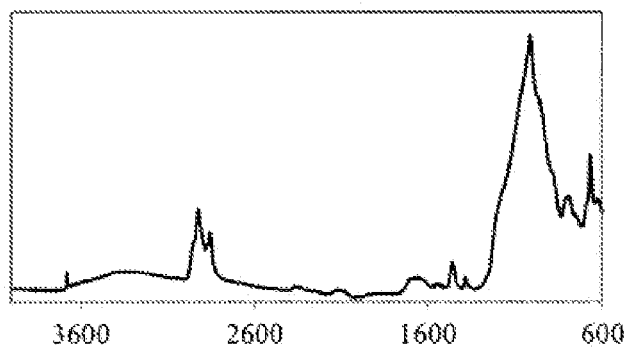

The FTIR spectrum of the porous silicon nanoparticles grafted with a porphyrin-NH$_2$ is shown in FIG. 13. In particular, two bands characteristic of the urea bond are observed at 1620 cm$^{-1}$ and 1542 cm$^{-1}$, attributed respectively to the stretching vibration of the C═O bond and the stretching vibration of the N—H bond, which indicates the success of the coupling between the nanoparticles functionalized with isocyanate and porphyrin-NH$_2$.

The quantification of the grafted porphyrin-NH$_2$ carried out by dissolution of the nanoparticles in a basic KOH solution indicates that a quantity of 13.3 μg porphyrin per mg nanoparticles is obtained. This quantity is sufficient for PDT applications.

2. Production of $^1O_2$ (oxygen) and of ROS (reactive oxygen species). The measurements consist of irradiating a photosensitizer in the presence of a probe molecule, diphenylisobenzofuran (DPBF), the oxidation of which by $^1O_2$ manifests itself as a decrease in the absorption spectrum. It is a comparative method: from knowing the quantum yield of $^1O_2$ generation of a reference molecule (such as rose bengal or methylene blue), that of the functionalized porous silicon nanoparticles is deduced by spectrophotometric monitoring.

Experimental: 2 mL of a solution of DPBF at 0.08 mM and of nanoparticles (or photosensitizing molecule) at a known concentration is placed in a quartz vessel. The vessel is stirred, closed and irradiated for 15 min. The irradiation is carried out with an optical fibre 0.63 cm in diameter. The light is filtered through an anti-IR filter so as not to heat up the sample, and a band-pass filter between 410 and 490 nm (Figure IV.1). The absorbance of the solution is measured every minute for the first 5 minutes, then every 5 minutes.

Figure 15:
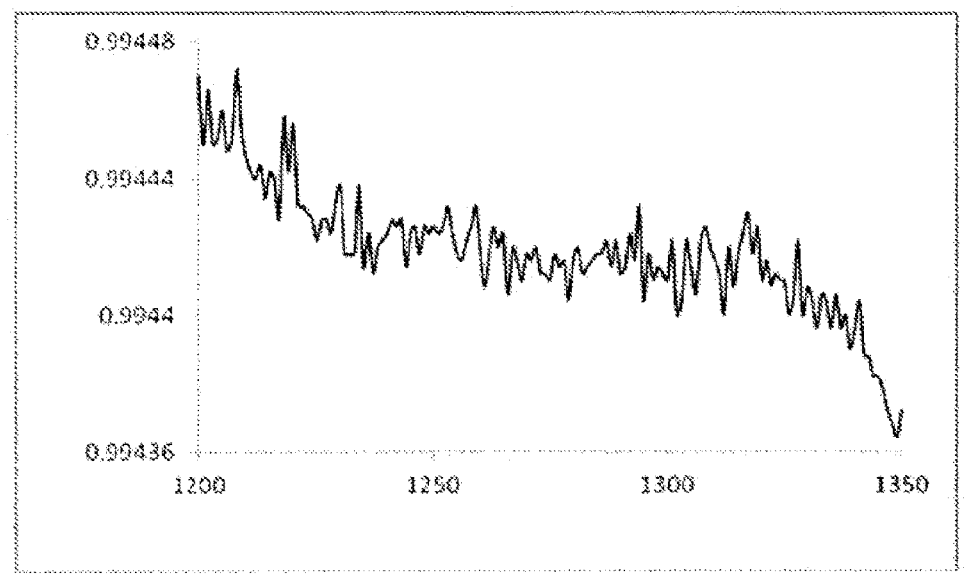
Figure 16:
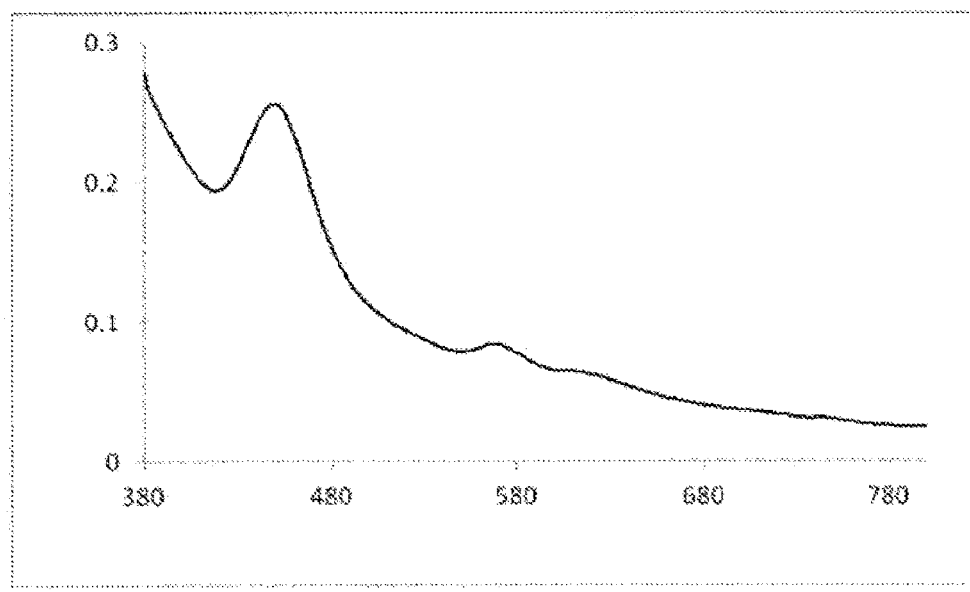
Figure 17:
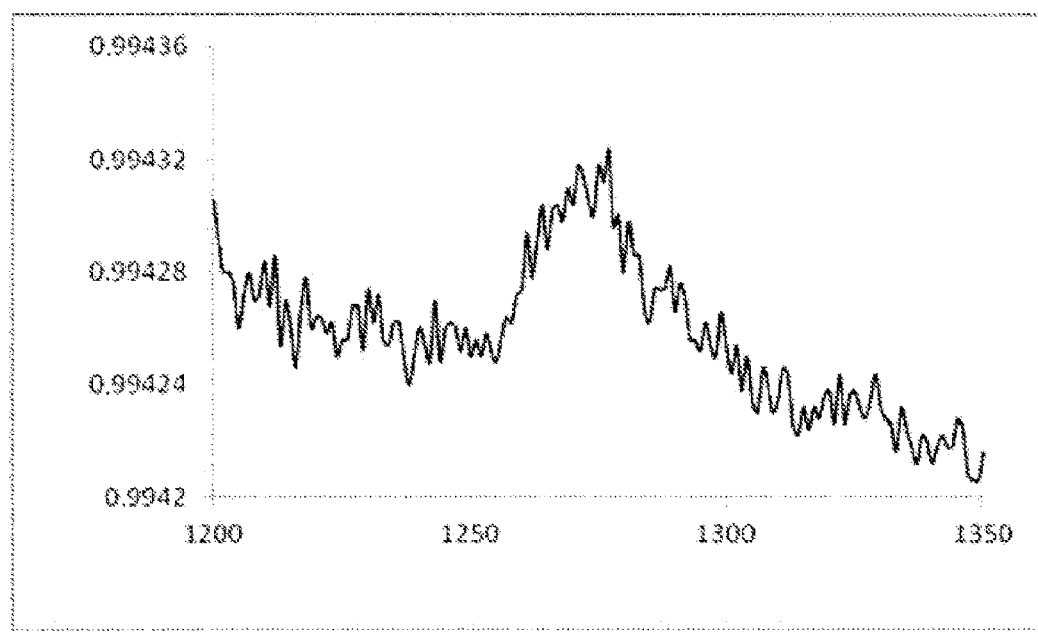
Figure 23:
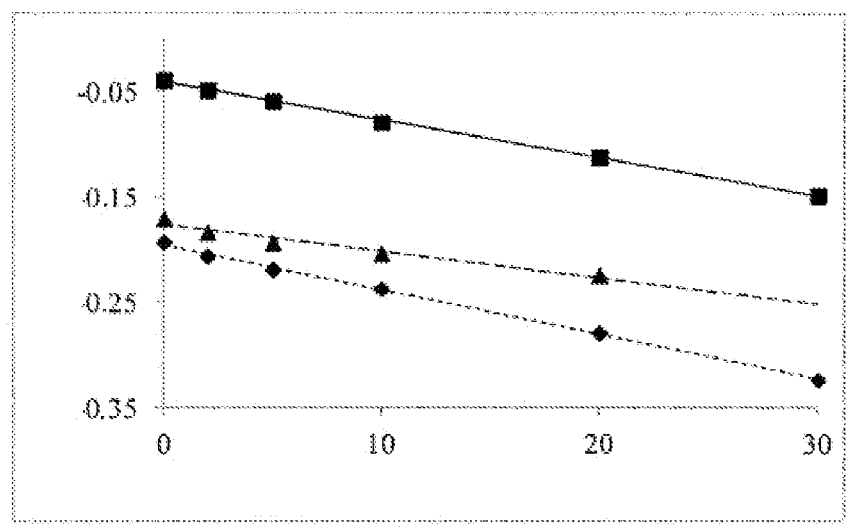
Figure 24:
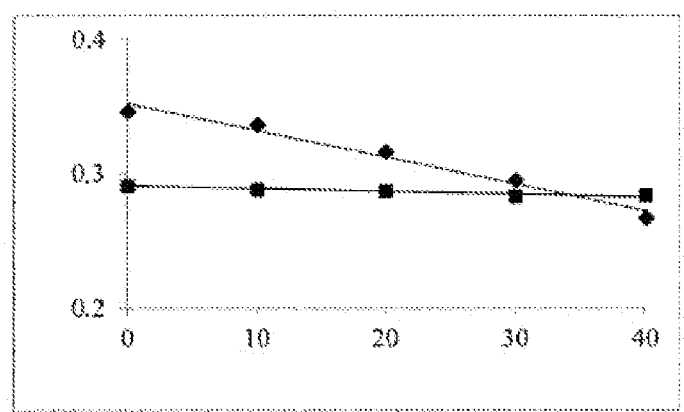

No production of singlet oxygen is observed for the porous Si nanoparticles that do not contain porphyrin (FIG. 15). A production of singlet oxygen is observed for the porous Si nanoparticles functionalized with porphyrin-NCS (FIG. 23), for the porous Si nanoparticles functionalized with porphyrin-NH$_2$ (FIG. 24) and for the porous Si nanoparticles functionalized with porphyrin-NCS of mannose (FIG. 17).

Figure 25:
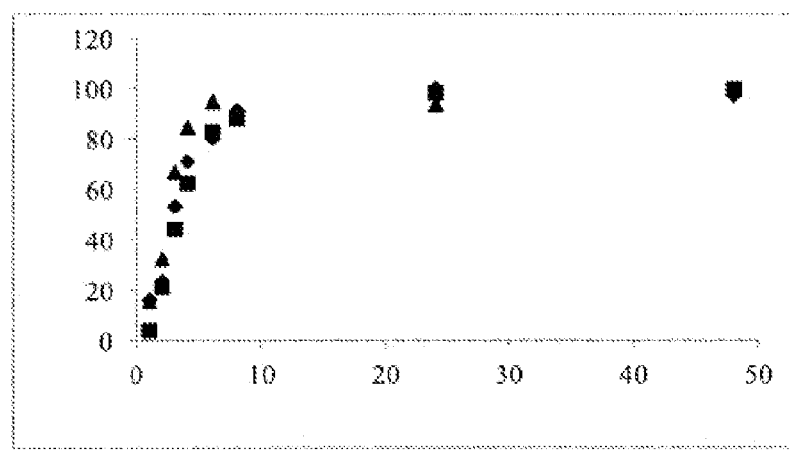
Figure 26:
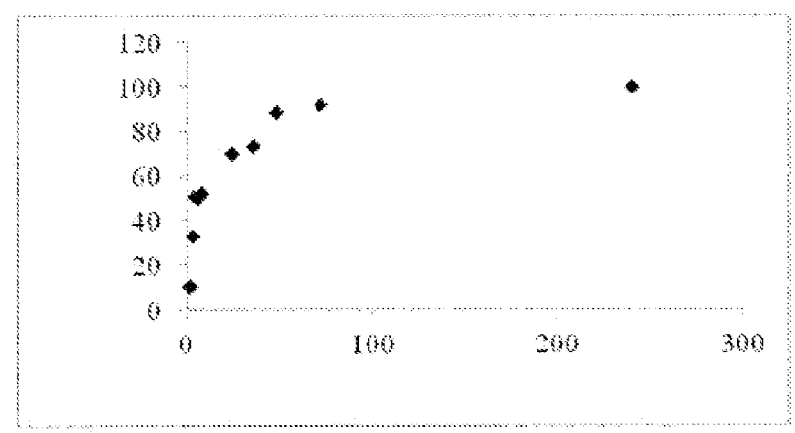

3. Release Kinetics of the Porphyrins (FIGS. 25, 26)

Experimental: The release of porphyrin as a function of time was studied in PBS (phosphate buffer saline) at pH=7.2, in DMEM F12 culture medium without serum and in DMEM F12 culture medium at 10% FBS (fetal bovine serum). A known quantity of grafted nanoparticles (approximately 500 μg) is dispersed in 3 mL of medium and incubated at 37° C. on a stir plate at 100 rpm. At given times, 500 μL of each dispersion is removed and 500 μL of the study medium is added so as to keep the volume constant. The 500 μL of dispersion removed is centrifuged at 22000 g for 30 min. The supernatant is kept away from light at 4° C. until analysis, the nanoparticle pellet is redispersed in the study medium.

The removed samples are analyzed by UV-visible absorption spectroscopy in order to determine the porphyrin concentration of each sample. The presence of mannose on the surface of the porous silicon nanoparticles does not influence their degradation kinetics. The porous silicon nanoparticles are completely degraded after 24 h of incubation in biological medium, they are biodegradable.

4. Targeting of Tumours and "Homing"

Figure 18:
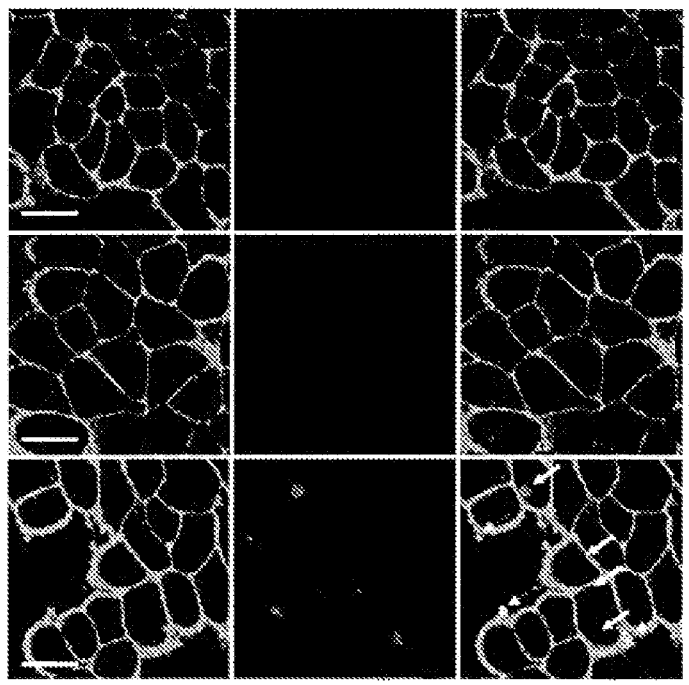

4.1 Imaging in Monophotonic Excitation Mode with the Porous Silicon Nanoparticles Grafted with Porphyrin-NH$_2$ (FIG. 18)

Experimental: The MCF-7 cells are seeded in glass-bottomed wells at a density of $10^6$ cells/cm$^2$. After 24 hours they are rinsed once then incubated in 1 mL of culture medium containing the porous silicon nanoparticles at a concentration of 20 μg/mL, and/or the free porphyrin at an equivalent concentration for 3 or 5 h depending on the experiments. Fifteen minutes before the end of the incubation, the cell membranes are labelled with Cell Mask Orange (Invitrogen) at a final concentration of 5 μg/mL (for the experiment with the nanoparticles grafted with porphyrin-NH$_2$ only). They are then rinsed with white DMEM culture medium (without phenol red). The microscopy photos are taken on an LSM 780 LIVE confocal microscope. The fluorescence excitation is carried out at 405 nm or at 633 nm depending on the samples. The emission is collected between 620 and 700 nm.

Figure 27:
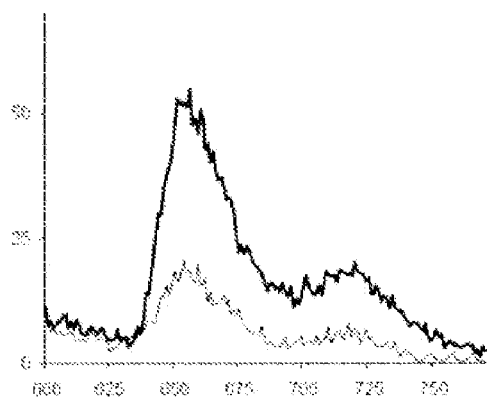
Figure 28:
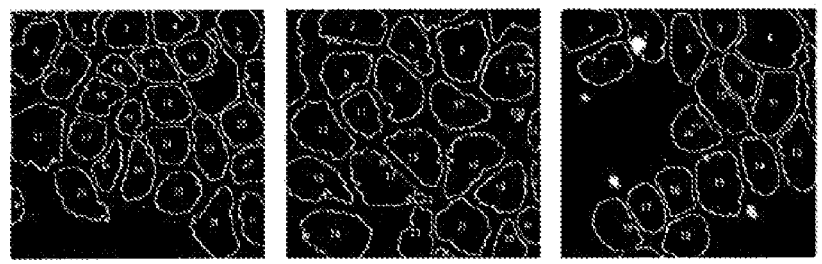
Figure 28:
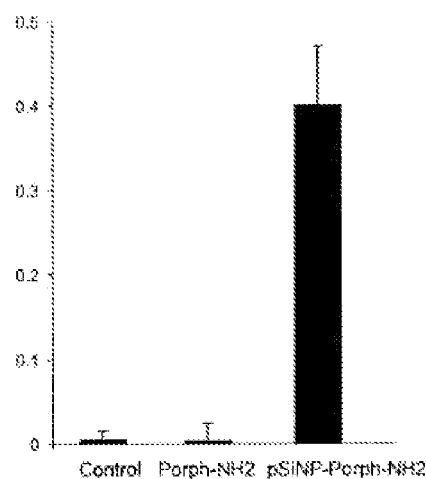

FIG. 18 also shows that free porphyrin-$NH_2$ is not detected inside the cell, whereas the nanoparticles grafted to porphyrin-$NH_2$ are internalized and appear luminescent. This experiment shows that the use of porous silicon nanoparticles is an effective means for internalizing porphyrin-$NH_2$ in the cells. The quantity of porphyrin internalized from the nanoparticles is in the range 105±5 ng·ml−1 porphyrins, whereas the free porphyrin internalized corresponds to 35±5 ng·ml−1 (FIG. 27 and FIG. 28).

Figure 29:
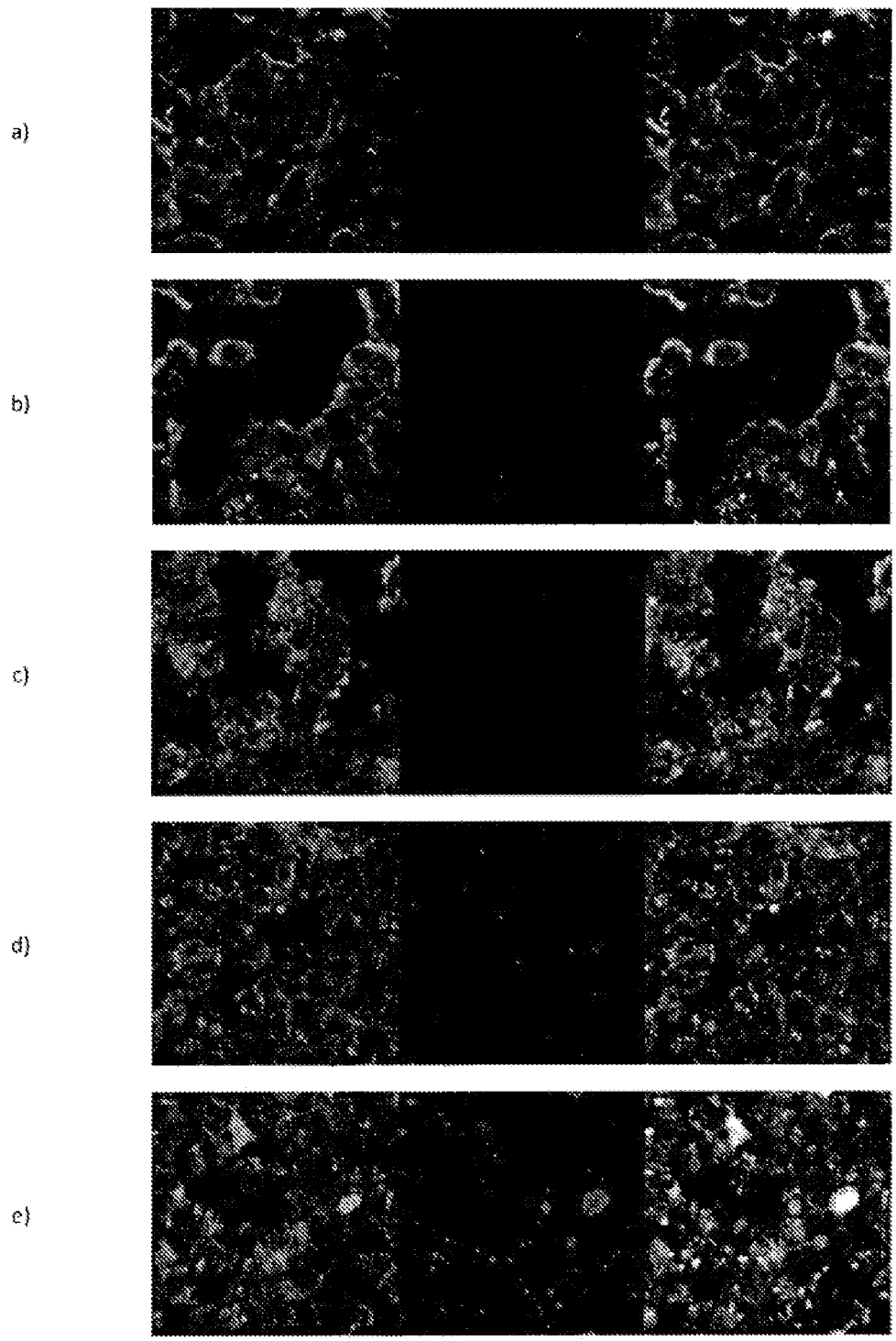

4.2 Imaging in Monophotonic Excitation Mode with the Porous Silicon Nanoparticles Grafted with Porphyrin-NCS (FIG. 29)

When the MCF-7 cells are incubated with the porous silicon nanoparticles grafted with porphyrin-NCS, distinct points of fluorescence are observed on the surface or in the cells. This result confirms the possibility of internalizing porphyrin in MCF-7 cells by means of porous silicon nanoparticles, even without a targeting agent. This internalization is possible through the action of clathrins and the formation of invagination vesicles. When the MCF-7 cells are incubated with the nanoparticles grafted with porphyrin and mannose, intense fluorescence aggregates are observed inside the cells. The porous silicon nanoparticles grafted with porphyrin-NCS and mannose are therefore present to a considerably greater extent than the porous silicon nanoparticles grafted with porphyrin-NCS without mannose: the mannose here plays its role of targeting agent with great effectiveness. It is thought that the mannose on the surface of the nanoparticles ensures the endocytosis thereof by the cells.

Similar results can be obtained by functionalizing the porous Si with galactose species.

Figure 30:
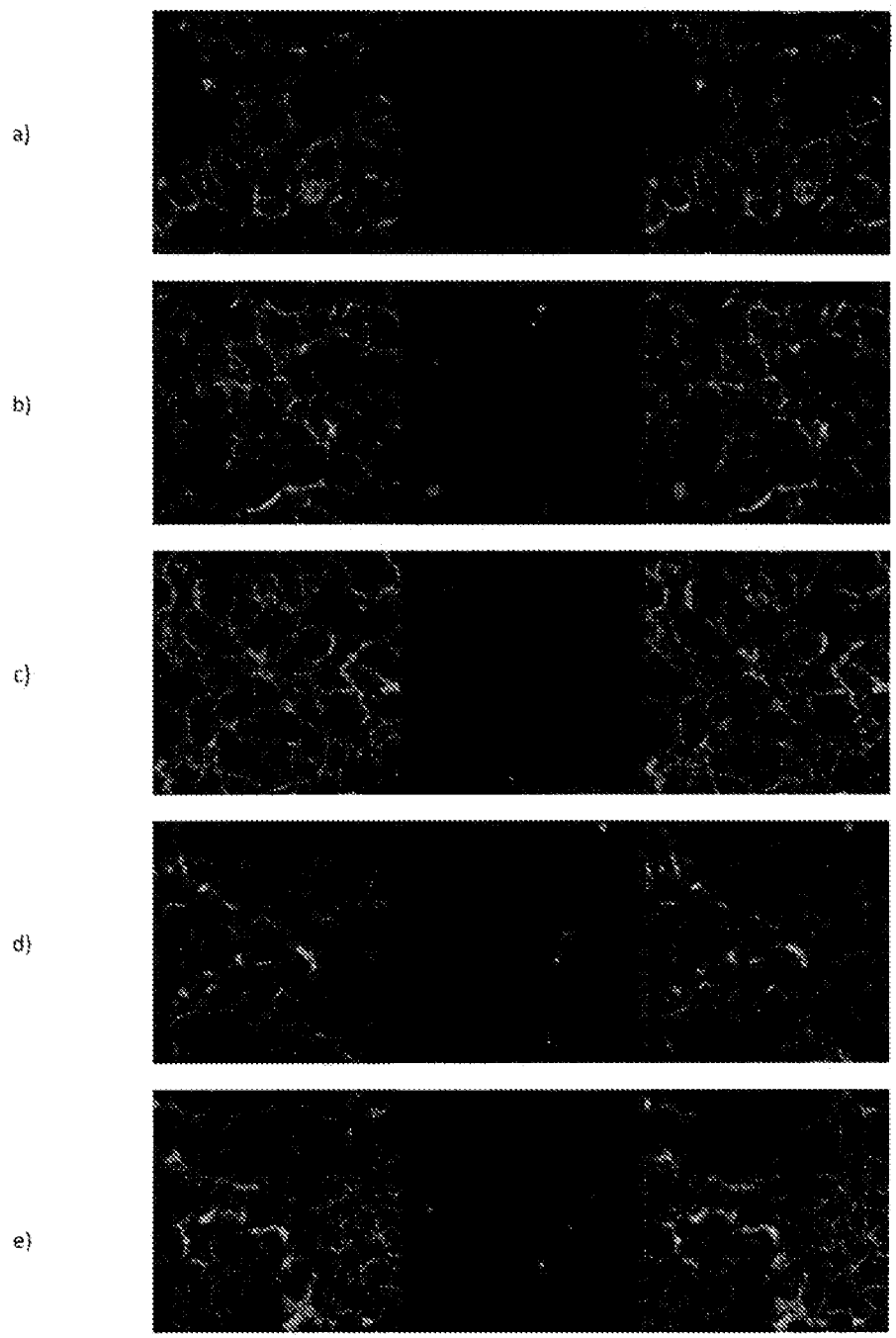
Figure 30:
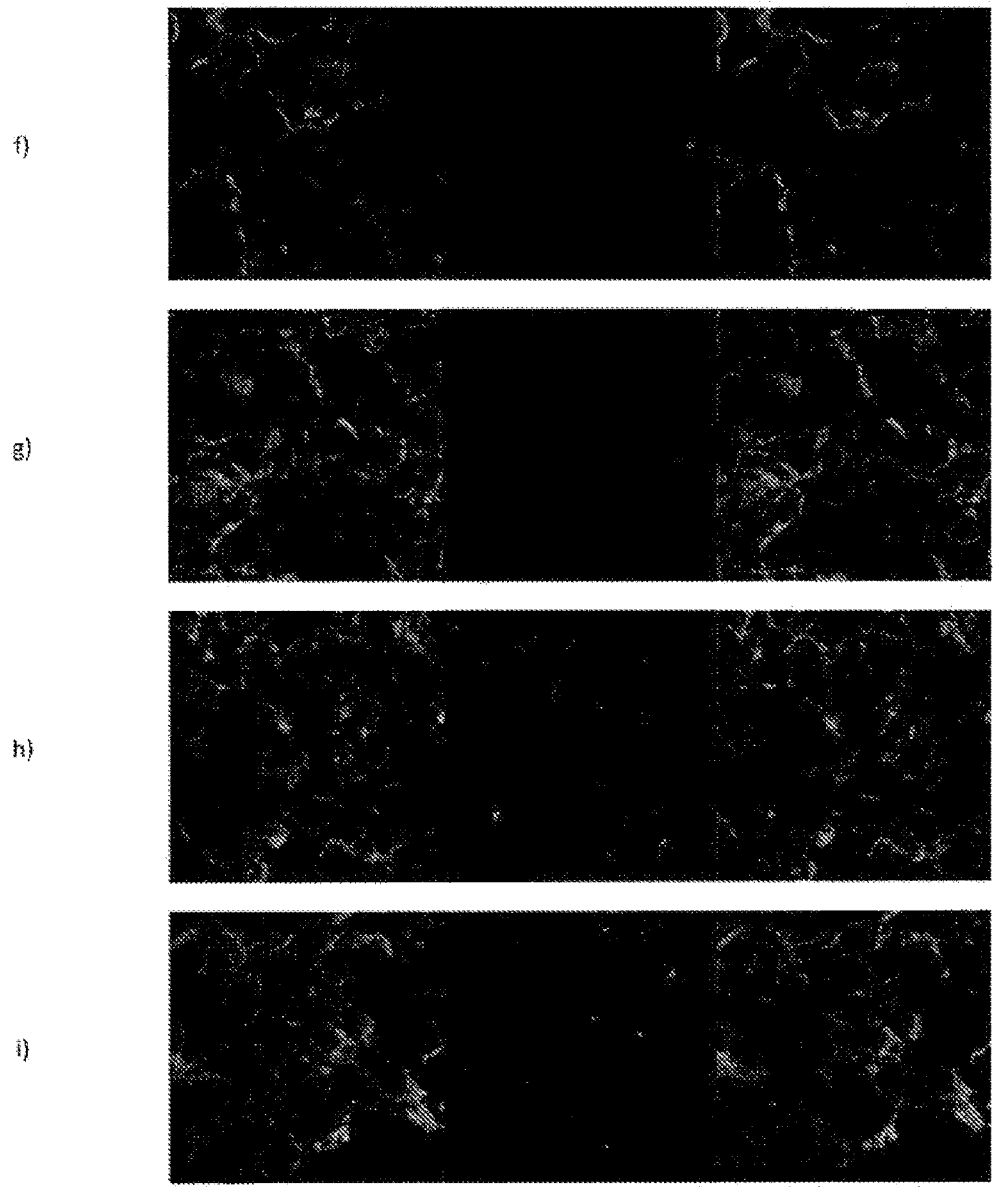

4.3 Imaging in Biphotonic Excitation Mode with the Porous Silicon Nanoparticles Grafted with Porphyrin-NCS (FIG. 30A and FIG. 30B)

Experimental: the MCF-7 cells were incubated for 5 h with the different types of nanoparticles: pSiNP, pSiNP-porphyrin-NCS, pSiNP-mannose, pSiNP-mannose-porphyrin-NCS at 40 μg/mL. The MCF-7 cells were also incubated for 5 h with free porphyrin-NCS at 3.2 μg/mL, with pSiNP and free porphyrin, as well as with pSiNP-mannose and pSiNP-mannose-porphyrin-NCS with free mannose (at a concentration of 10 mM) in order to study the reversion of the targeting by mannose. The cells were then rinsed, then imaged after excitation with a biphotonic pulsed laser at 750 nm. A membrane dye was added so as to identify the cells. The development was carried out in confocal mode.

When the cells are incubated with the porous silicon nanoparticles, a few fluorescent zones are observed, indicating that these nanoparticles can be internalized, even if it appears that this only happens in quite small proportions. Moreover, the observation of the fluorescence here indicates that porous silicon can absorb light in biphotonic mode.

By comparison, when the MCF-7 cells are incubated with free porphyrin-NCS, no fluorescence is observed after biphotonic excitation at 750 nm. This means that the porphyrin-NCS present on/in the cells after rinsing, which could be distinguished by imaging in monophotonic excitation mode (at 650 nm), is not excited in biphotonic light at 750 nm.

When the cells are incubated with the mannose-porphyrin-NCS porous silicon nanoparticles, the fluorescence observed is much greater than with the other types of nanoparticles. The fluorescence is also intracellular, which indicates an internalization of the nanoparticles which is clearly improved by the presence of the mannose on their surface. When the same experiment is carried out in the presence of an excess of free mannose in the culture medium, a blockage of the internalization of the nanoparticles is observed which is characterized by a fluorescence that is more membranous than intracellular.

The fluorescence observed in biphotonic excitation mode for each type of nanoparticles can be classified according to the following scale: free porphyrin-NCS<pSiNP~pSiNP-mannose~pSiNP+free porphyrin-NCS<pSinp-porphyrin-NCS<pSiNP-mannose-porphyrin-NCS.

The results obtained here show that, as in monophotonic imaging mode, the presence of the mannose allows a better internalization of the porous silicon nanoparticles. The combined presence of porphyrin-NCS and mannose on the surface of the porous silicon nanoparticles makes it possible to optimize their internalization in the cells and their visualization by biphotonic imaging. A joint action mechanism between silicon and the grafted porphyrin-NCS, of the energy-transfer type, is envisaged for the emission of the fluorescence of the pSiNP grafted with porphyrin.

4.4 Photodynamic Efficacy in Monophotonic Excitation Mode

Figure 31:
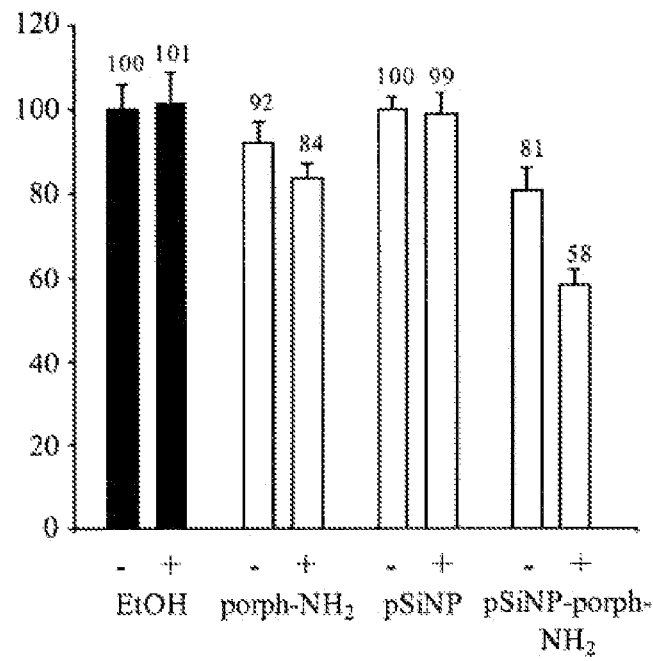

Experimental: The MCF-7 cells are seeded in a 96-well plate, at a density of $10^6$ cells/$cm^2$. After 24 h, the cells are incubated with the porous silicon nanoparticles at a concentration of 20 μg/mL or 40 μg/mL for the nanoparticles grafted respectively with porphyrin-$NH_2$ and porphyrin-NCS, or with free porphyrin at an equivalent concentration for 5 h. The cells are then rinsed with PBS, then kept in 100 μL of culture medium, and finally irradiated for 40 min with a laser at 650 nm with a power of 7 mW/$cm^2$ (i.e. 16.8 J/$cm^2$). After incubation for 48 h, an MTS assay (3-(4,5-dimethylthiazol-2-yl)-5-(3-carboxymethoxyphenyl)-2-(4-sulphophenyl)-2H-tetrazolium) is carried out in order to quantify the living cells in the experiment with the porous silicon nanoparticles grafted with porphyrin-NCS. In the case of the nanoparticles grafted with porphyrin-$NH_2$, an MTT assay (3-(4,5-dimethylthiazol-2-yl)-2,5-diphenyltetrazolium bromide) is carried out in order to quantify the living cells. In the case of the MTT assay, the cells are incubated for 4 h in culture medium supplemented with 0.5 mg/mL MTT. The medium is then removed and the purple MTT crystals are dissolved in an ethanol/DMSO (1:1) solution. The absorbance of the solution is read at 540 nm. In the case of the MTS assay, the cells are incubated for 2 h in culture medium supplemented with 0.5 mg/mL MTS. The absorbance of the solution is then read directly at 490 nm 4.4.1 Porphyrin-$NH_2$ (FIG. 31)

Irradiation of the cancer cells alone does not induce any toxicity. The porous silicon nanoparticles (pSiNP) are not cytotoxic, 99% and 100% of the cells remain alive after incubation for 5 h with or without irradiation respectively. The fact that the pSiNP are not cytotoxic after irradiation at 650 nm was expected, taking into account the fact that the pSiNP do not absorb light at this wavelength.

Porphyrin-$NH_2$ induces 8% cytotoxicity in the absence of irradiation. After irradiation, a slightly higher cell death rate (16%) is observed. This quite low cytotoxicity of the free porphyrin after irradiation was expected, because the imaging and quantification experiments showed that the free porphyrin-$NH_2$ was poorly internalized by the cells. By comparison, the cells incubated with the pSiNP-porphyrin-$NH_2$ and not irradiated have a cell death of 19%. In this case, the observed toxicity in the dark is attributed to the release of a small quantity of cytotoxic porphyrin-NH$_2$ inside the cell, after the internalization and the poor metabolization of the nanoparticles. Finally, the pSiNP-porphyrin-NH$_2$ induce a cell death of 42% after irradiation at 650 nm. The toxicity of the porphyrin-NH$_2$ confined in the porous silicon nanoparticles is therefore significantly increased compared with the free porphyrin-NH$_2$.

Figure 32:
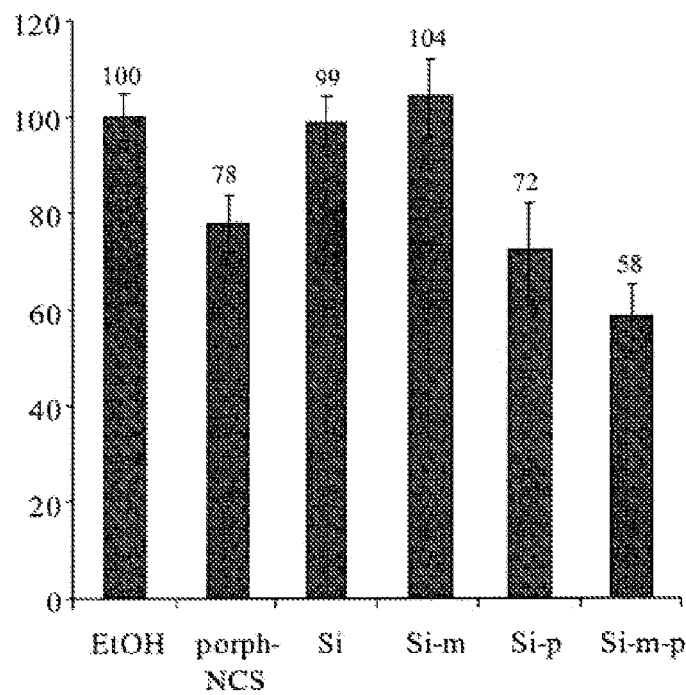

4.4.2 Porphyrin-NCS (FIG. 32)

The pSiNP and the pSiNP-mannose, irradiated at 650 nm, are not toxic for the cells. 99% and 104% of the MCF-7 cells respectively survive after incubation for 5 hours with pSiNP functionalized or not functionalized with mannose and after irradiation. In a parallel experiment, the toxicity of the pSiNP at different concentrations without irradiation was studied on the same cells. At 40 µg/mL, the porous silicon nanoparticles are of very low toxicity without irradiation for the cells.

After incubation of the free porphyrin-NCS and irradiation, a cell death of 22% is observed. Sufficient porphyrin-NCS adheres to the membranes and/or is internalized by the cells, as was seen in the confocal microscopy images, to generate a not insignificant effect in monophotonic PDT.

By comparison, the cells treated with the pSiNP-porphyrin-NCS show a cell death of 28%. The effect of the porphyrin-NCS vectorized by the nanoparticles here is not significantly increased compared with the effect of the free porphyrin. By contrast, during the treatment by PDT of the MCF-7 cells with the pSiNP-mannose-porphyrin-NCS, the cell survival rate falls to 58%. The increase in cytotoxicity and in the efficacy of the PDT observed here is attributed to a more effective targeting of the cells thanks to the presence of the mannose, as well as to a greater internalization or anchoring to the surface of the cells than for the pSiNP-porphyrin-NCS, in accordance with the imaging experiments.

4.5 Photodynamic Effectiveness in Biphotonic Excitation Mode

A particularly useful approach consists of replacing the conventional one-photon excitation in the visible range with a two-photon excitation in the near-infrared range, because this makes it possible to limit the side effects due to light in the tissues treated by photodynamic therapy. The advantage of a two-photon excitation is also that this makes it possible to treat cancers in deeper tissues.

Figure 19:
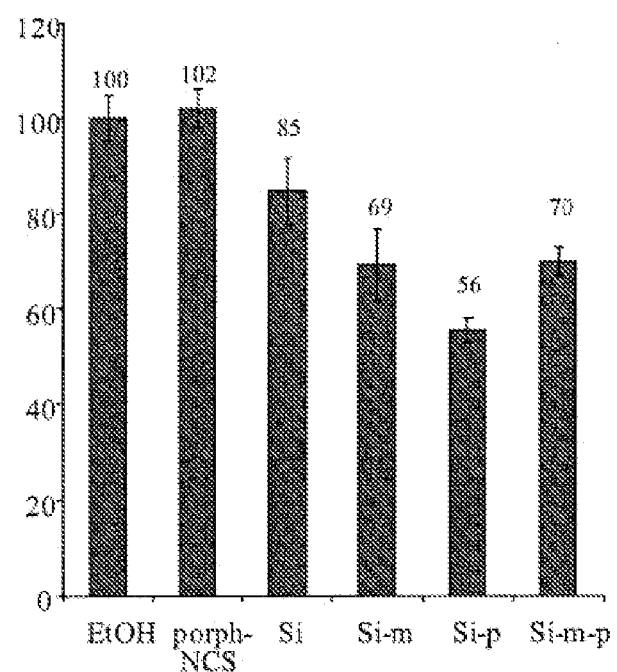
Figure 20:
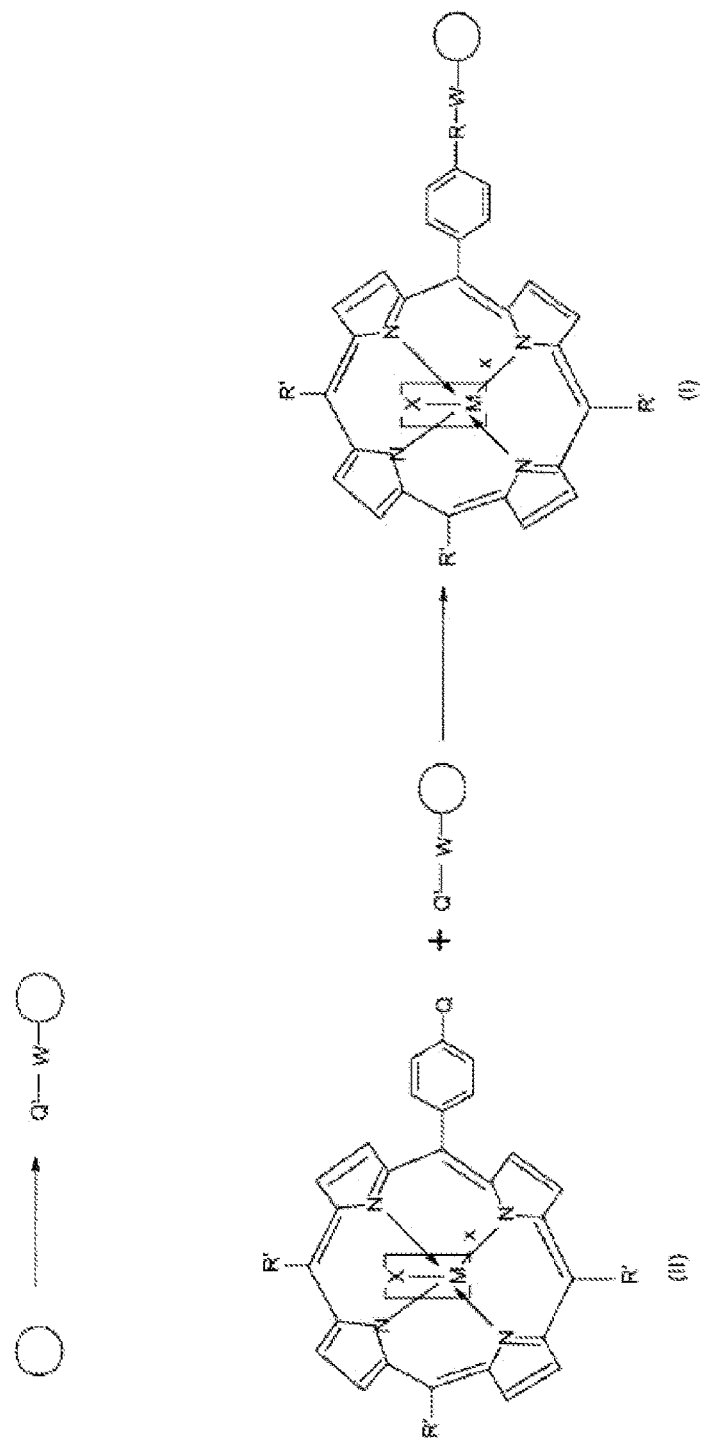
Figure 21A:
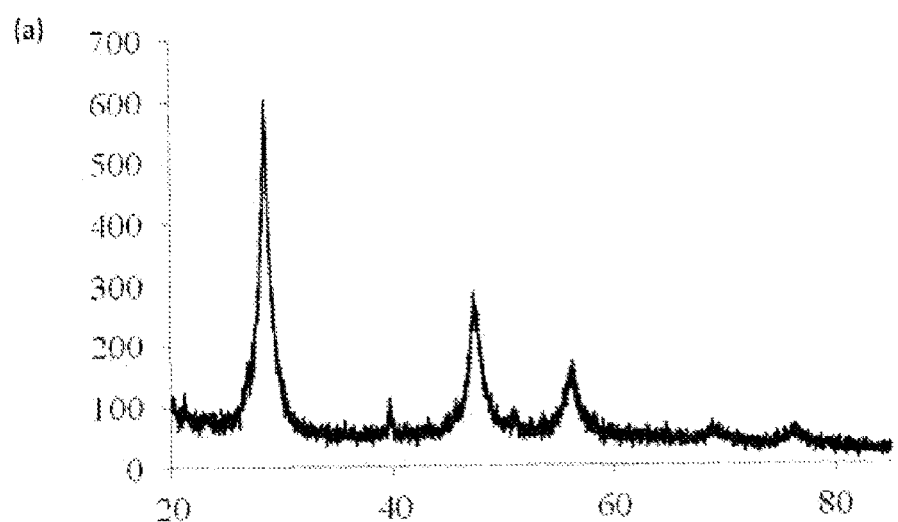
FIGS. 21A and 21B show the X-ray powder diffractograms at wide angles and at narrow angles for the porous Si nanoparticles shown in FIG. 3.
Figure 21B:
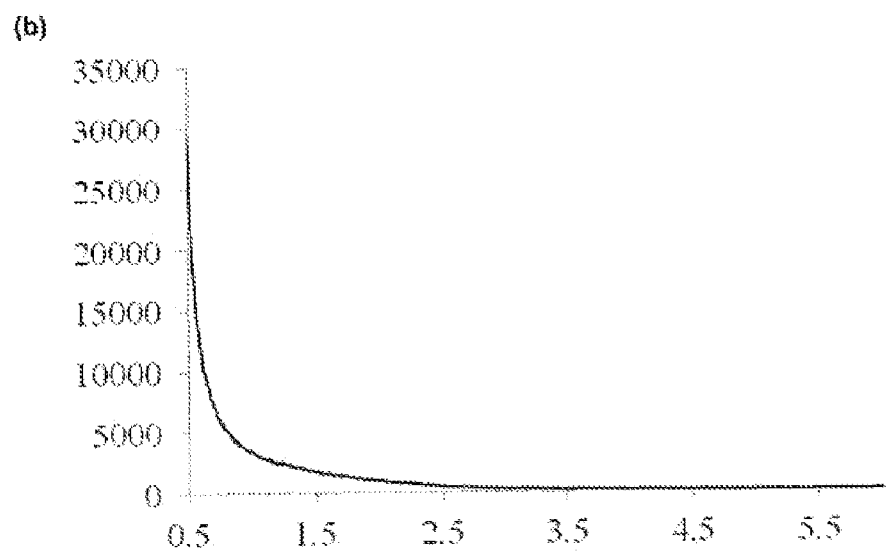

One of the inventors has shown previously that porous silicon nanoparticles can be excited by an excitation in 2-photon mode in the near infrared (780 nm). Here, in an experiment on 2-photon PDT, it is shown that the porous Si nanoparticles containing a polycationic porphyrin excited in 2-photon mode (750 nm) can kill cancer cells after endocytosis of the nanoparticles (FIG. 19).

Experimental: The MCF-7 cells are seeded in a 384-well plate, at a density of 10$^6$ cells/cm$^2$. After 24 h, the cells are incubated with the porous silicon nanoparticles at a concentration of 40 µg/mL, or with free porphyrin at a concentration of 3.2 µg/mL for 5 h. The cells are then rinsed (this rinsing step not having been carried out for certain control experiments), then irradiated with a biphotonic laser at 750 nm. 3 scans of 1.57 s are carried out. After incubation for 48 h, an MTS assay is carried out in order to quantify the living cells.

The cells incubated in the control culture medium alone and irradiated do not display any cell death, which indicates that neither the culture medium containing ethanol nor the biphotonic irradiation are toxic for the cells. Nor is any cell death observed when the MCF-7 cells are incubated with free porphyrin-NCS, rinsed, then irradiated. Contrary to what was observed under monophotonic irradiation, the porphyrin-NCS remaining on the cells after rinsing is not sensitive to biphotonic excitation and therefore is not toxic for the cells.

When the MCF-7 cells are treated with the non-functionalized pSiNP, a cell death of 15% is observed after rinsing and biphotonic irradiation. This result indicates that the pSiNP, which are capable of absorbing biphotonic light, generate $^1O_2$ or other ROS and kill the cells. However, the effect observed here is quite weak. This result can be explained by two reasons: it is known that the quantum yield of $^1O_2$ generation of the porous silicon is quite low on the one hand; on the other hand it has been observed in the imaging experiments that the internalization of the pSiNP was not very high. By comparison, it can be observed that the nanoparticles, when they are functionalized with mannose (pSiNP-mannose), kill 31% of cells after irradiation. The presence of mannose grafted to the surface of the nanoparticles seems to allow a better internalization in the cells. After incubation of the cellules with the pSiNP-porphyrin-NCS, rinsing and biphotonic irradiation, a cell death of 44% is observed.

The hypothesis being made here is based on the possibility of an energy transfer between the pSiNP, which are sensitive to biphotonic excitation, and the porphyrin-NCS.

This result suggests a mechanism of FRET (fluorescence resonance energy transfer) in 2-photon excitation mode from the porous Si nanoparticles to the porphyrins and, as a result, the generation of singlet oxygen and reactive oxygen species under 2-photon irradiation.

Figure 33:
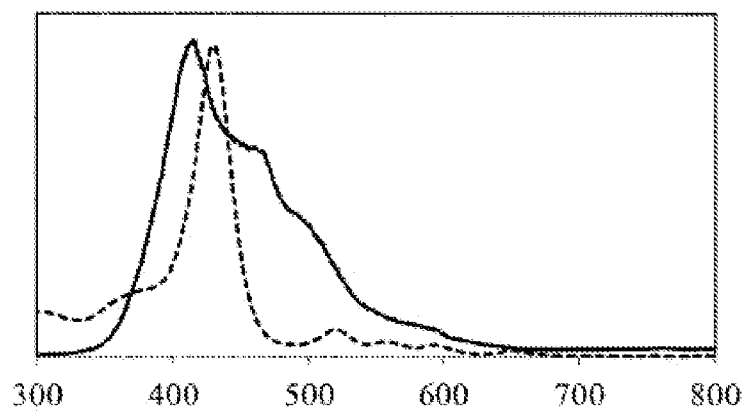

The conditions needed for such a transfer, defined by the Forster-Dexter theory, are that the two systems, donor and acceptor, silicon and porphyrin respectively in this case, be close enough to each other in space (the distance between the two must not exceed 10 nm), and that the emission spectrum of the donor and the absorption spectrum of the acceptor at least partially overlap. In the case in point, the proximity of the silicon and the porphyrin is ensured by the covalent grafting. Using Chem3D software, the distance between the silicon and the porphyrin was estimated at 7.8 Å, which is much less than the limit distance that allows the energy transfer. Moreover, the overlap of the emission spectrum of the donor and the absorption spectrum of the acceptor is shown in FIG. 33.

Finally, when the MCF-7 cells are incubated with the pSiNP-mannose-porphyrin-NCS, the cell death rate observed is 30%. This result is surprising. In fact, there was expected to be a maximum cell death rate for these nanoparticles because, on the one hand, the quantity of grafted porphyrin is greater than on the nanoparticles grafted only with porphyrin and, on the other hand, the presence of mannose-squarate on the surface of the nanoparticles improves the internalization of the nanoparticles by the cells. However, these nanoparticles have a lesser effect in 2-photon PDT than the nanoparticles grafted with porphyrin. Given the hypothesis of the energy transfer between the pSiNP and the porphyrin-NCS, this is explained by the absorption of some of the transmitted energy by the mannose. In fact, the mannose, in order to be grafted to the surface of the pSiNP, has a phenyl group and a squarate group. The aromaticity and the conjugation of the squarate are suspected of being at the origin of a deactivation of the excited state of the porous silicon, and explains this absorption of the energy. Another type of bond for the mannose, such as a ketone, described previously can be used for the grafting of the mannose.

Of course the present invention is not limited to the examples and embodiment described and shown, but is capable of numerous variants accessible to a person skilled in the art.

This application was filed first in a foreign country without the knowledge or consent of the Regents of the University of California, and this was done in error and without the intention to deceive.

The invention claimed is:

1. Nanoparticles corresponding to formula (I):

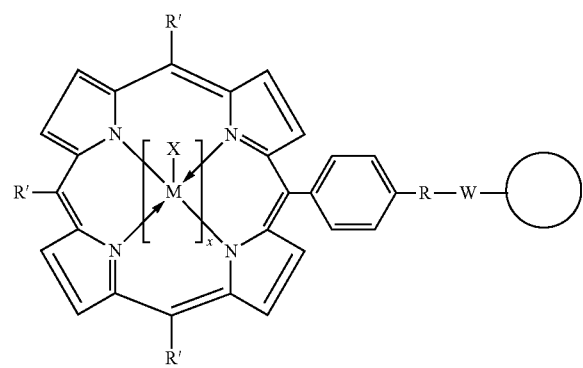
(I)

in which:

represents a porous silicon nanoparticle, x represents 0 or 1,

M represents a transition metal atom,

X represents a halide or an anion of a pharmaceutically acceptable carboxylic acid, R represents a urea (—NH—CO—NH—) or a thiourea (—NH—CS—NH—), W represents a C1-C12 alkanediyl group, R' represents:

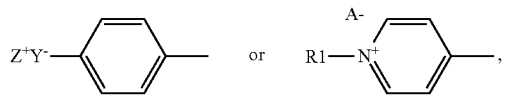

$Z^+$ represents a pharmaceutically acceptable organic or mineral cation, $Y^-$ represents —COO$^-$ or —SO$_3^-$, $A^-$ represents a halide or an anion of a pharmaceutically acceptable carboxylic acid, and R1 represents a C1 to C10 alkyl group.

2. The nanoparticles according to claim 1 corresponding to formula (Ia):

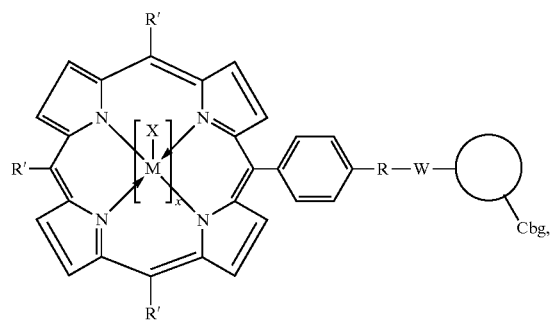
(Ia)

wherein Cbg represents a specific targeting molecule for neoplastic tissues.

3. The nanoparticles according to claim 2, the size of which is from 20 to 200 nm.

4. The nanoparticles according to claim 2, in which x represents 0.

5. The nanoparticles according to claim 2, in which:

X represents a group selected from the group consisting of: Cl$^-$, Br$^-$, I$^-$, acetate, propionate, butyrate, ascorbate, benzoate, cinnamate, citrate, fumarate, glycolate, malonate, tartrate, malate, maleate, mandelate, and tosylate, W represents a —(CH$_2$)$_3$— group, R' is:

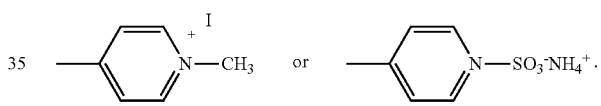

and

Cbg is selected from the group consisting of folic acid, peptides, carbohydrates and antibodies.

6. A method for producing nanoparticles according to claim 2, said method comprising the steps of:

(i) providing porous silicon nanoparticles, (ii) functionalizing the porous silicon nanoparticles with groups comprising at least one C1-C12 NH$_2$ function or at least one C1-C12 isocyanate or C1-C12 isothiocyanate, (iii) providing and grafting a porphyrin-type photosensitizing molecule corresponding to formula (II),

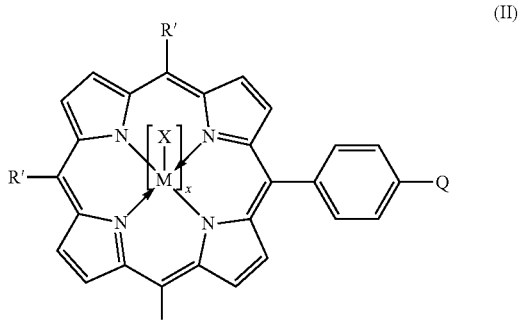
(II)

in which:

x represents 0 or 1,

M represents a transition metal atom,

X represents a halide or an anion of a pharmaceutically acceptable carboxylic acid, Q represents a group selected from the group consisting of —$NH_2$, —N=C=O, and —N=C=S, R' represents:

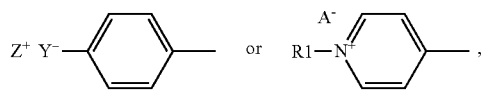

$Z^+$ represents a pharmaceutically acceptable organic or mineral cation, $Y^-$ represents —$COO^-$ or —$SO_3^-$, $A^-$ represents a halide or an anion of a pharmaceutically acceptable carboxylic acid, and R1 represents a C1 to C10 alkyl group, and optionally (iv) grafting with at least one targeting molecule.

7. The nanoparticles according to claim 1, the size of which is from 20 to 200 nm.

8. The nanoparticles according to claim 7, in which x represents 0.

9. The nanoparticles according to claim 7, in which:

X represents a group selected from the group consisting of: $Cl^-$, $Br^-$, $I^-$, acetate, propionate, butyrate, ascorbate, benzoate, cinnamate, citrate, fumarate, glycolate, malonate, tartrate, malate, maleate, mandelate, and tosylate, W represents a —$(CH_2)_3$— group, R' is:

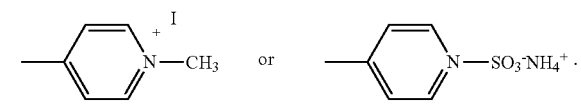

10. The nanoparticles according to claim 1, in which x represents 0.

11. The nanoparticles according to claim 10, in which:

X represents a group selected from the group consisting of: $Cl^-$, $Br^-$, $I^-$, acetate, propionate, butyrate, ascorbate, benzoate, cinnamate, citrate, fumarate, glycolate, malonate, tartrate, malate, maleate, mandelate, and tosylate, W represents a —$(CH_2)_3$— group, R' is:

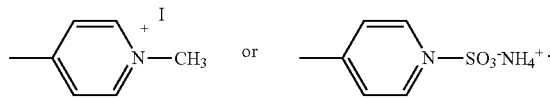

12. The nanoparticles according to claim 1, in which:

X represents a group selected from the group consisting of: $Cl^-$, $Br^-$, $I^-$, acetate, propionate, butyrate, ascorbate, benzoate, cinnamate, citrate, fumarate, glycolate, malonate, tartrate, malate, maleate, mandelate, and tosylate, W represents a —$(CH_2)_3$— group, and R' is:

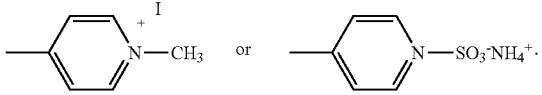

13. The nanoparticles according to claim 12, wherein the nanoparticles have a structure according to one of:

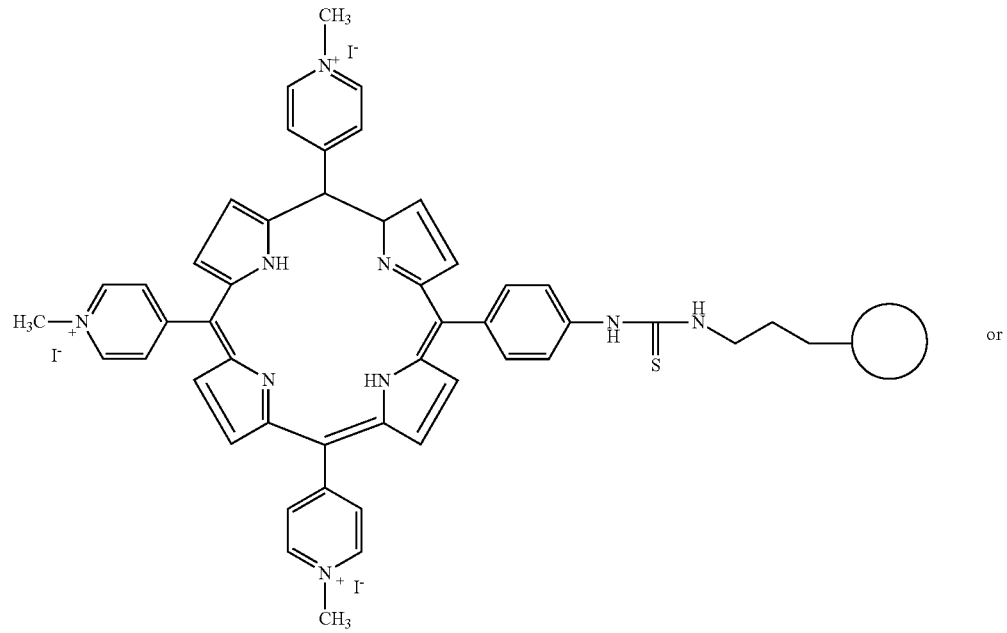

or

-continued

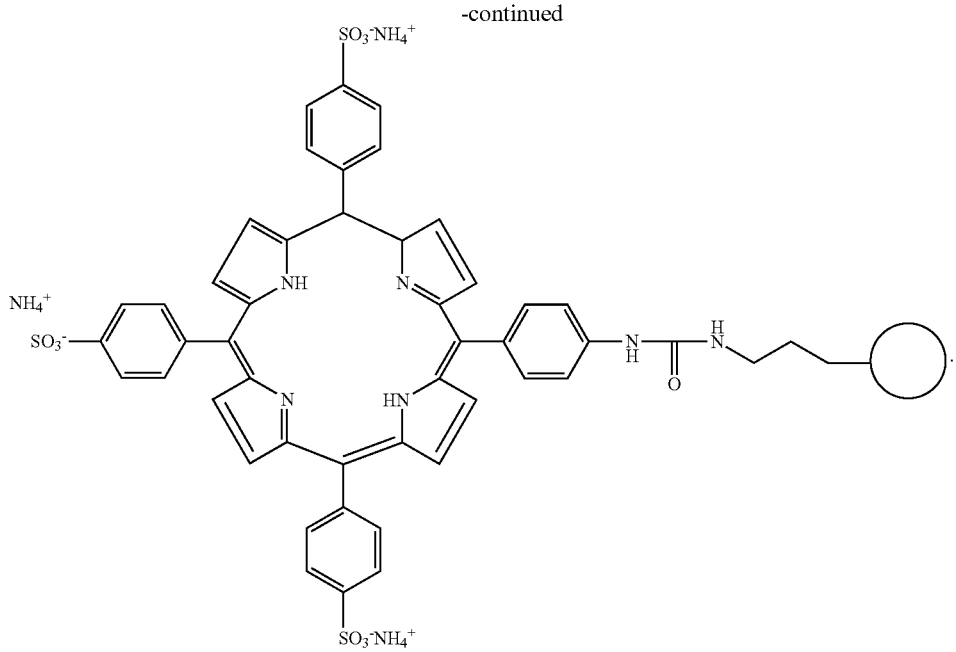

14. A method for producing nanoparticles according to claim 1, said method comprising the steps of:
   (i) providing porous silicon nanoparticles,
   (ii) functionalizing the porous silicon nanoparticles with groups comprising at least one C1-C12 $NH_2$ function or at least one C1-C12 isocyanate or C1-C12 isothiocyanate, and
   (iii) providing and grafting a porphyrin-type photosensitizing molecule corresponding to formula (II),

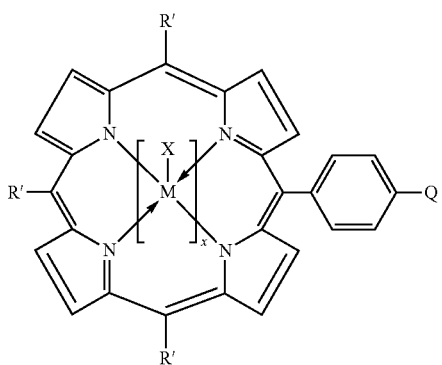

in which:
   x represents 0 or 1,
   M represents a transition metal atom,
   X represents a halide or an anion of a pharmaceutically acceptable carboxylic acid,
   Q represents a group selected from the group consisting of —$NH_2$, —N=C=O, and —N=C=S, R' represents:

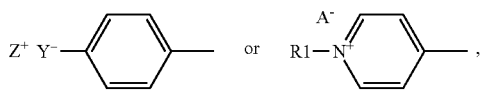

$Z^+$ represents a pharmaceutically acceptable organic or mineral cation,
   $Y^-$ represents —$COO^-$ or —$SO_3^-$,
   $A^-$ represents a halide or an anion of a pharmaceutically acceptable carboxylic acid, and
   R1 represents a C1 to C10 alkyl group.

15. The method according to claim 14, which comprises the steps of:
   (i) a—electrochemical etching of monocrystalline silicon plates in a hydrofluoric (HF) ethanol solution,
      b—removal of the porous film and treatment by ultrasound,
   (ii) a—controlled oxidation followed by silanization so as to produce Si—OH groups and $SiO_2$ species on the surface of the porous silicon nanoparticles, and treatment by an aminoalkylsilanyl group, and/or
      b—hydrosilylation with a C1-C12 allylamine, C1-C12 allyl isocyanate or C1-C12 allyl isothiocyanate, and
   (iii) grafting the porous nanoparticles of step (ii) with a porphyrin-type photosensitizing molecule corresponding to formula (II).

16. A medicinal composition comprising nanoparticles according to claim 1 in a pharmaceutically acceptable support.

17. A cosmetic composition comprising nanoparticles according to claim 1 in a cosmetically acceptable support.

18. A kit for the detection, treatment, monitoring, prevention, and delay of the appearance and/or recurrence of a pathology selected from the group consisting of cancers, tumors, and cell proliferation diseases, comprising:
   nanoparticles according to claim 1, and
   means that allow an irradiation in the infrared.

* * * * *